(12) United States Patent
Abele et al.

(10) Patent No.: US 11,547,568 B2
(45) Date of Patent: Jan. 10, 2023

(54) IMPLANT AND KIT FOR TREATING A BONE DEFECT

(71) Applicant: Aesculap AG, Tuttlingen (DE)

(72) Inventors: Wolfgang Abele, Tuttlingen (DE); Georg Hettich, Tuttlingen (DE); Silke Koenig, Rottweil (DE)

(73) Assignee: AESCULAP AG, Tuttlingen (DE)

( * ) Notice: Subject to any disclaimer, the term of this patent is extended or adjusted under 35 U.S.C. 154(b) by 294 days.

(21) Appl. No.: 16/461,658

(22) PCT Filed: Nov. 15, 2017

(86) PCT No.: PCT/EP2017/079312
§ 371 (c)(1),
(2) Date: May 16, 2019

(87) PCT Pub. No.: WO2018/091524
PCT Pub. Date: May 24, 2018

(65) Prior Publication Data
US 2019/0350713 A1    Nov. 21, 2019

(30) Foreign Application Priority Data

Nov. 16, 2016   (DE) ..................... 10 2016 222 603.7

(51) Int. Cl.
*A61F 2/28*     (2006.01)
*A61L 27/12*    (2006.01)
(Continued)

(52) U.S. Cl.
CPC ............ *A61F 2/2846* (2013.01); *A61L 27/12* (2013.01); *A61L 27/20* (2013.01); *A61L 27/22* (2013.01);
(Continued)

(58) Field of Classification Search
CPC combination set(s) only.
See application file for complete search history.

(56) References Cited

U.S. PATENT DOCUMENTS 5,133,970 A * 7/1992 Petereit ............... A61K 9/7061
424/443
5,711,960 A   1/1998 Shikinami
(Continued)

FOREIGN PATENT DOCUMENTS

DE   10 2012 213 246    1/2014
EP         0764008      3/1997
(Continued)

OTHER PUBLICATIONS

Honnami et al., "Bone Regeneration by the Combined Use of Tetrapod-Shaped Calcium Phosphate Granules with Basic Fibroblast Growth Factor-Binding Ion Complex Gel in Canine Segmental Radial Defects." (2014) J. Vet. Med. Sci. 76(7):1955-961.
(Continued)

*Primary Examiner* — Yashita Sharma
(74) *Attorney, Agent, or Firm* — Lewis Kohn & Walker LLP; David M. Kohn

(57) ABSTRACT

An implant for treating a bone defect wherein the implant comprises osteoconductive supporting bodies and an insertion aid. The insertion aid is designed for insertion of the osteoconductive supporting bodies into a bone defect and for holding together the osteoconductive supporting bodies. Also disclosed is a kit comprised of an implant for treating a bone defect.

15 Claims, 12 Drawing Sheets

(51) Int. Cl.
*A61L 27/20* (2006.01)
*A61L 27/22* (2006.01)
*A61F 2/30* (2006.01)

(52) U.S. Cl.
CPC . *A61F 2002/285* (2013.01); *A61F 2002/2835* (2013.01); *A61F 2002/3069* (2013.01); *A61F 2002/30273* (2013.01); *A61F 2002/30275* (2013.01); *A61F 2002/30303* (2013.01); *A61F 2002/30448* (2013.01); *A61F 2002/30593* (2013.01); *A61F 2310/00293* (2013.01); *A61L 2430/02* (2013.01)

(56) References Cited

U.S. PATENT DOCUMENTS

| | | |
|---|---|---|
| 7,731,756 B2 | 6/2010 | Maspero et al. |
| 8,562,613 B2 | 10/2013 | Ahern et al. |
| 10,201,338 B1* | 2/2019 | Pacifico ............... A61L 24/046 |
| 10,751,443 B2 | 8/2020 | Grupp et al. |
| 2003/0039676 A1* | 2/2003 | Boyce ............... A61L 31/005 |
| | | 424/423 |
| 2003/0049328 A1* | 3/2003 | Dalal ............... A61L 27/56 |
| | | 424/602 |
| 2004/0249471 A1 | 12/2004 | Bindseil et al. |
| 2005/0196432 A1* | 9/2005 | Munro ............... A61L 15/425 |
| | | 424/445 |
| 2009/0010988 A1 | 1/2009 | Chung et al. |
| 2010/0143490 A1 | 6/2010 | Roberts et al. |
| 2010/0209470 A1* | 8/2010 | Mohan ............... A61K 35/32 |
| | | 424/423 |
| 2010/0286702 A1 | 11/2010 | Ahern et al. |
| 2011/0027381 A1* | 2/2011 | Gradl ............... A61K 38/39 |
| | | 424/602 |
| 2014/0276994 A1 | 9/2014 | Nguyen |
| 2015/0127106 A1 | 5/2015 | Partee et al. |

FOREIGN PATENT DOCUMENTS

| | | |
|---|---|---|
| EP | 1408888 | 4/2004 |
| JP | 2008284302 | 11/2008 |
| WO | 2012061024 | 5/2012 |

OTHER PUBLICATIONS

English translation of First Office Action dated May 17, 2021, of corresponding Chinese Patent Application No. 201780083697.5.
Japanese Office Action dated Sep. 7, 2021, of corresponding Japanese Patent Application No. 2019-547184.

* cited by examiner

IMPLANT AND KIT FOR TREATING A BONE DEFECT

FIELD OF APPLICATION AND PRIOR ART

The invention relates to an implant and a kit for treating a bone defect.

Large bone defects of the acetabulum constitute a major problem in revision surgery of the hip joint. In hip revision surgery, the three primary goals are as follows.

First, the original joint center must be restored.

Another goal is stable fixation of an implant used for treating a bone defect. In fixation of the implant, a distinction is generally made between so-called primary stability and so-called secondary stability.

Primary stability is understood to refer to fixation of the implant in the first few weeks after the operation due to friction or fastening elements such as e.g. bone screws. Secondary stability is understood to refer to fixation of the implant based on bony adhesions. Secondary stability is ordinarily achieved about one month after surgery and can last up to several years.

A final goal is so-called biological reconstruction of the bony defects. Biological reconstruction is understood to refer to rebuilding of a bone defect using endogenous bone.

The two options described below have become accepted in practice for the treatment of bone defects.

The first option uses metallic augmentation materials, for example in the form of metallic porous structures. The use of metallic augmentation materials is advantageous in that the original joint center can ordinarily be favorably restored. In addition, good fixation of the implant can be achieved. A drawback, however, is that metallic augmentation materials remain unchanged in the body, with the result that biological reconstruction of bony defects does not occur. Moreover, in the case of a (repeated) revision, the entire augmentation material must be replaced, which ordinarily enlarges the defect. This applies in particular in the case of bony adhesions to the metallic augmentation material. A further drawback is that metallic augmentation materials are not moldable. This in turn means that the defect must be adapted to the augmentation material, which ordinarily also causes enlargement of the defect. An additional drawback is that metallic augmentation materials are not processable, with the result that the augmentation material cannot be used as a base for the structure implanted in the case of a (repeated) revision.

The second option for the fixation of implants used for the treatment of bone defects is the use of bone chips or shavings. Bone chips or shavings are advantageous in that they allow reconstruction of bony defects. As a rule, restoration of the center of rotation poses no problems. However, a drawback is the surgical handling of bone chips or shavings. The bone material must ordinarily be provided during surgery. For this purpose, an allogeneic femoral head is thawed and comminuted. Handling is made more difficult by the irregular shapes of the bone particles. The surgeon must therefore have considerable experience in order to correctly use these bone filling materials. Because bone banks are also subject to strict requirements, it is extremely complex and costly overall to obtain bone chips or shavings. A further drawback is the potential risk of infection. A final disadvantage is that bone chips or shavings are generally characterized by only limited mechanical load-bearing capacity (poor primary stability). There is also a risk that resorption will occur without any bone growth having set in or taken place. In other words, there is a certain risk that it will not be possible to achieve secondary stability.

U.S. Pat. No. 8,562,613 B2 discloses a kit for treating bone defects with a mixture of an osteoconductive material and an osteoinductive material and a porous container.

The subject matter of EP 0764008 B1 is a device for use in stabilizing a spinal motion segment with a flexible bag, wherein the bag can contain a biological filler material for promoting bone or fiber adhesion.

EP 1408888 B1 discloses a system for correcting spinal compression fractures that comprises a porous bag and a filling tool, wherein the filling tool is designed to inject a bone filling material under pressure into the porous bag.

WO 2012/061024 A1 discloses an implantable container that contains at least partially demineralized and osteoinductive bone particles.

The publication "Bone Regeneration by the Combined Use of Tetrapod-Shaped Calcium Phosphate Granules with Basic Fibroblast Growth Factor-Binding Ion Complex Gel in Canine Segmental Radial Defects (J. Vet. Med. Sci. 76(7):955-961, 2014)" by Honnami et al. concerns a combination of tetrapod-shaped granules of alpha-tricalcium phosphate and an osteoinductive gel.

Object and Means for Achieving Object

The object of the invention is to provide an implant that is suitable for treating a bone defect, in particular a periprosthetic bone defect, that avoids or at least largely avoids the above-mentioned drawbacks, in particular in connection with hip revision surgery. The implant is to have sufficient mechanical stability such as primary and/or secondary stability, and should optionally allow biological reconstruction of a bony defect and be as simple as possible to handle. In particular, the implant is to be suitable for meeting all three of the requirements mentioned in connection with hip revision surgery (primary stability, secondary stability and biological reconstruction).

This object is achieved by means of an implant with the features described in the specification. Preferred embodiments are defined in the claims. The wording of all of the claims is incorporated by reference in its entirety into the content of the present description. In addition, the invention relates to a method for treating a bone defect. Further objects of the invention are disclosed in the description.

According to a first aspect, the invention relates to an implant, preferably for the treatment and/or biological reconstruction, in particular lining and/or sealing and/or packing and/or at least partial filling, of a bone defect. The implant is preferably a surgical implant.

The implant comprises the following or consists of the following:

osteoconductive supporting bodies and an insertion aid.

The implant is characterized in particular in that the insertion aid is configured for insertion of the osteoconductive supporting bodies into a bone defect and for holding together, in particular holding together permanently or temporarily, of the osteoconductive supporting bodies, preferably during and/or after their insertion into a bone defect.

The term "bone defect" refers within the meaning of the present invention to a bone area affected by loss of bone tissue, in particular articular bone tissue, preferably hip joint or knee joint bone tissue, or vertebral bone tissue, in particular the articular bone area, preferably the hip joint or knee joint bone area, or the vertebral area. The bone loss can be the result of a bone fracture, a bone trauma, a bone disease such as neoplastic disease, or surgical intervention/ reintervention, in particular a revision after a total hip or knee joint replacement. Preferably, the term "bone defect" within the meaning of the present invention refers to a periprosthetic bone defect, i.e. a bone area affected by periprosthetic bone tissue loss, in particular tissue loss due to mechanical overloading and/or wear-induced osteolysis and/or implant migration.

Preferably, the bone defect is an articular bone defect, in particular a knee joint bone defect or a hip joint bone defect, and preferably an acetabular defect.

Moreover, the term "bone defect" within the meaning of the present invention can refer to a human bone defect or an animal bone defect.

The term "animal bone defect" is to be understood within the meaning of the present invention as referring to a bone defect in a non-human mammal, such as e.g. a horse, cow, goat, sheep, pig or a rodent such as e.g. a rabbit, rat or mouse.

The term "supporting bodies" refers within the meaning of the present invention to bodies, in particular regularly and/or irregularly formed bodies, which are designed to withstand the forces ordinarily occurring in a bone defect to be treated without deformation or destruction, or at least without substantial deformation or destruction, and thus to take over load-bearing functions. For this reason, the supporting bodies within the meaning of the present invention can also be referred to as osteoconductive, weight-bearing supporting bodies.

The term "osteoconductive" used in connection with the supporting bodies refers within the meaning of the present invention to the capacity of the supporting bodies to form a three-dimensional structure, in particular a guide structure, or a three-dimensional matrix, in particular guide matrix, which facilitates the growing in of bone tissue, in particular new bone tissue.

The term "insertion aid" refers within the meaning of the present invention to a means designed to insert osteoconductive supporting bodies into a bone defect and to hold osteoconductive supporting bodies together, in particular permanently or temporarily, preferably during and/or after insertion of the osteoconductive supporting bodies into a bone defect. The insertion aid can within the meaning of the present invention therefore also be referred to as an insertion means.

Within the meaning of the present invention, the term "osteoactive and in vivo degradable/in vivo resorbable" means osteoactive and in vivo degradable or osteoactive and in vivo resorbable.

The term "osteoactive" preferably refers within the meaning of the present invention to a so-called osteogenic material, i.e. a material that stimulates or enhances the growth of (already present) bone tissue, and/or to a so-called osteoinductive material, i.e. a material that stimulates or enhances the neoformation (so-called neogenesis) of bone tissue. In particular, the term "osteoactive" can refer to a material that has osteoactive and osteoinductive properties.

The term "in vivo degradable" refers within the meaning of the present invention to a substance or a material that can be metabolized in a human or animal body, in particular under the action of enzymes. The degradation of the substance or material can take place all the way to the occurrence of mineralization, i.e. the release of chemical elements and their incorporation into inorganic compounds, such as e.g. carbon dioxide, oxygen and/or ammonia, or stop at the stage of degradation-resistant intermediate or transformation products.

The term "animal body" is to be understood within the meaning of the present invention as referring to the body of a non-human mammal, such as e.g. a horse, cow, goat, sheep, pig or a rodent such as e.g. a rabbit, rat or mouse.

The term "in vivo resorbable" refers within the meaning of the present invention to a substance or a material that can be absorbed in a human or animal body by living cells or living tissue, such as e.g. the kidneys, without the occurrence of degradation or significant degradation of the material.

The term "sheath" is to be understood within the meaning of the present invention as referring to a structure or construct that is configured to completely surround or enclose (at least) the osteoconductive supporting bodies. For this purpose, the sheath preferably comprises a hollow space that is at least partially, preferably only partially, Tillable or filled with (at least) the osteoconductive supporting bodies.

The present invention is characterized in particular by the following advantages:

During a favorable course of healing, the osteoconductive supporting bodies can in a particularly advantageous manner be incorporated into endogenous bone or undergo cellular conversion. In this manner, biological reconstruction of a bone defect can be ensured. In patients with slow bone growth, the osteoconductive supporting bodies are preferably retained, at least until sufficient secondary stability has been achieved. This is particularly advantageous with respect to older patients, in whom bone growth often no longer takes place.

A further advantage is that the osteoconductive supporting bodies, in a compacted, preferably impacted (clamped or wedged-in), state, can act as a placeholder and/or a guide structure to allow bone tissue, in particular new bone tissue, to grow into the implant and in particular into a bone defect to be treated.

A further advantage is that the implant, in particular when the osteoconductive supporting bodies are in a compacted, preferably impacted, state, can be permanently and above all homogenously loaded. Homogeneous implant loading is a basic prerequisite for bone growth. For example, the implant, in particular with osteoconductive supporting bodies that are in a compacted, preferably impacted state, can be loaded long-term with a pressure load of up to 10 MPa. Here, a structure formed by compaction, in particular impaction, and produced by the osteoconductive supporting bodies, can particularly advantageously show elastic deformation, in particular of 5% to 15%, and a low E modulus, in particular of 50 MPa to 300 MPa.

In contrast to generic implants, in particular metallic augmentation materials, in which only intermediate spaces in the edge areas of the implant are mechanically loaded, when the osteoconductive supporting bodies are in a compacted state, hollow and/or intermediate spaces present, because of the low E modulus, can be mechanically loaded within a complete defect filling, i.e. homogenously (micromovements). This in turn results in stimulation and/or enhancement of bone growth, in particular bone regeneration. Overall, this makes it possible to achieve homogeneous ossification of the entire bone defect.

By means of the insertion aid, insertion of the osteoconductive supporting bodies into a bone defect to be treated and thus in particular the operative handling of the implant is facilitated in a particularly advantageous manner for a user, preferably a surgeon.

A further advantage of the insertion aid is in particular that it prevents unwanted dislocation or dispersion of the osteoconductive supporting bodies within a bone defect to be treated, in particular during surgery, by holding the osteoconductive supporting bodies together. In other words, the insertion aid makes it possible to achieve local binding of the osteoconductive supporting bodies within a bone defect to be treated, thus allowing their osteoconductivity and the above advantages mentioned in connection with the supporting bodies to be manifested in a particularly favorable manner. For example, the insertion aid allows as complete compaction, in particular impaction, as possible of the supporting bodies after insertion into a bone defect, without uncontrolled dispersion of at least a part of the supporting bodies during compaction, in particular impaction, within the bone defect. In this manner, the supporting bodies make it possible to build up a particularly effective osteoconductive guide structure, which in turn is essential for sufficient secondary stability and in particular for biological reconstruction.

The implant according to the invention is suitable in particular for the biological reconstruction of large bone defects, in particular bone defects requiring a load stability up to a pressure of up to 10 MPa.

In a preferred embodiment, the osteoconductive supporting bodies comprise apatite and/or tricalcium phosphate or consist of apatite and/or tricalcium phosphate. The present invention is based in particular on the surprising finding that the advantages mentioned above in connection with the osteoconductive supporting bodies are particularly enhanced when the supporting bodies comprise apatite and/or tricalcium phosphate or consist of apatite and/or tricalcium phosphate.

In a further embodiment, the osteoconductive supporting bodies comprise apatite or consist of apatite.

In a further embodiment, the apatite is a non-in vivo degradable/non-in vivo resorbable apatite. This allows sufficient secondary stability to be achieved even in patients in whom one can no longer expect (sufficient) bone growth. This is advantageous in particular in the treatment of bone defects in older patients.

In a further embodiment, the apatite is an in vivo degradable/in vivo resorbable apatite, preferably a slowly in vivo degradable/slowly in vivo resorbable apatite.

In a further embodiment, the apatite has an in vivo decomposition time (degradation time) or an in vivo resorption time of 6 months to 30 years, in particular 1 year to 20 years, and preferably 4 years to 10 years. The degradation or resorption times disclosed in this paragraph are particularly advantageous in the treatment of patients with slow bone growth.

In a further embodiment, the apatite is in crystalline form. High crystallinity allows high strength to be achieved. Low crystallinity allows good and/or rapid degradability to be achieved.

In a further embodiment, the apatite is a microcrystalline apatite, i.e. an apatite with crystallites having at least one measurement or dimension in the µm range, in particular in a range of >0.5 µm, in particular 0.6 µm to 500 µm, and preferably 0.6 µm to 100 µm. The at least one measurement or dimension can in particular be the length and/or width (thickness or height) and/or the diameter, in particular the average diameter, of the crystallites.

In general, however, the apatite can also be a macrocrystalline apatite.

In a further embodiment, the apatite is a nanocrystalline apatite, i.e. an apatite with crystallites having at least one measurement or dimension in the nm range, in particular in a range of 0.1 nm to 500 nm and preferably 0.1 nm to 100 nm. The at least one measurement or dimension can in particular be the length and/or width (thickness or height) and/or the diameter, in particular the average diameter, of the crystallites.

In a further embodiment, the apatite is in amorphous form. This allows particularly good and/or rapid resorption to be achieved.

In a further embodiment, the apatite is a phase-pure apatite. The term "phase-pure" is understood in particular to mean phase-pure in the sense of a relevant standard, preferably according to ASTM F1185.

In a further embodiment, the apatite has a porosity of less than 50%, in particular less than 20%, and preferably less than 15%. By means of low porosity, high mechanical stability can be achieved.

In a further embodiment, the apatite is not configured to be porous.

In particular, the supporting bodies can comprise a combination of porous apatites and/or apatites with varying porosity and/or nonporous apatites, in particular if the supporting bodies are produced according to an additive manufacturing method.

In a further embodiment, the apatite is naturally occurring apatite or an apatite obtained from natural apatite.

In a further embodiment, the apatite is a synthetic, i.e. man-made or artificial, apatite.

In a further embodiment, the apatite is selected from the group consisting of hydroxyapatite, fluorapatite, chlorapatite, carbonate-fluorapatite and mixtures of at least two of the aforementioned apatites.

Particularly preferably, the apatite is hydroxyapatite. For example, the hydroxyapatite can be a fully synthetic, nanocrystalline and phase-pure hydroxyapatite. Such a hydroxyapatite is commercially available, for example under the brand name Ostim or Nanogel.

In a further embodiment, the apatite is a sintered apatite. Preferably, the sintered apatite is selected from the group consisting of sintered hydroxyapatite, sintered fluorapatite, sintered chlorapatite, sintered carbonate-fluorapatite and mixtures of at least two of the aforementioned sintered apatites.

In a further preferred embodiment, the osteoconductive supporting bodies comprise tricalcium phosphate or consist of tricalcium phosphate.

In a further embodiment, the tricalcium phosphate is a non-in vivo degradable/non-in vivo resorbable tricalcium phosphate. This allows sufficient secondary stability to be achieved even in patients in whom one can no longer expect (sufficient) bone growth. This is advantageous in particular in treatment of bone defects in older patients.

In a further embodiment, the tricalcium phosphate is in vivo degradable/in vivo resorbable tricalcium phosphate, preferably a slowly in vivo degradable/slowly in vivo resorbable tricalcium phosphate.

In a further embodiment, the tricalcium phosphate has an in vivo decomposition time (degradation time) or an in vivo resorption time of 1 month to 15 years, in particular 6 months to 10 years, and preferably 1 year to 5 years. The degradation or resorption times disclosed in this paragraph are particularly advantageous in the treatment of patients with slow bone growth.

In a further embodiment, the tricalcium phosphate is in crystalline form. High crystallinity allows high strength to be achieved. Low crystallinity allows good and/or rapid degradability to be achieved.

Preferably, the tricalcium phosphate has a crystallinity of 50% to 99%, and in particular 75% to 95%.

In a further embodiment, the tricalcium phosphate is microcrystalline tricalcium phosphate, i.e. tricalcium phosphate with crystallites having at least one measurement or dimension in the μm range, in particular in a range of >0.5 μm, in particular 0.6 μm to 500 μm, and preferably 0.6 μm to 100 μm. The at least one measurement or dimension can in particular be the length and/or width (thickness or height) and/or the diameter, in particular the average diameter, of the crystallites.

In general, however, the tricalcium phosphate can also be a macrocrystalline tricalcium phosphate.

In a further embodiment, the tricalcium phosphate is a nanocrystalline tricalcium phosphate, i.e. a tricalcium phosphate with crystallites having at least one measurement or dimension in the nanometer range, in particular in a range of 0.1 nm to 500 nm, and preferably 0.1 nm to 100 nm. The at least one measurement or dimension can in particular be the length and/or width (thickness or height) and/or the diameter, in particular the average diameter, of the crystallites.

In a further embodiment, the tricalcium phosphate is in amorphous form. This allows particularly good and/or rapid resorption to be achieved.

In a further embodiment, the tricalcium phosphate is a phase-pure tricalcium phosphate. The term "phase-pure" is understood in particular to mean phase-pure within the meaning of a relevant standard, preferably according to ASTM F1088.

In a further embodiment, the tricalcium phosphate has a porosity of less than 50%, in particular less than 20%, and preferably less than 15%.

In a further embodiment, the tricalcium phosphate is not configured to be porous.

In a further embodiment, the tricalcium phosphate is a naturally occurring tricalcium phosphate or a tricalcium phosphate obtained from natural tricalcium phosphate.

In a further embodiment, the tricalcium phosphate is a synthetic, i.e. man-made or artificial, tricalcium phosphate.

The tricalcium phosphate is selected in a particularly preferred embodiment from the group consisting of alpha-tricalcium phosphate (α-TCP), beta-tricalcium phosphate (β-TCP) and a mixture of alpha-tricalcium phosphate and beta-tricalcium phosphate.

In a further embodiment, the tricalcium phosphate is sintered tricalcium phosphate.

The sintered tricalcium phosphate is preferably selected from the group consisting of sintered alpha-tricalcium phosphate, sintered beta-tricalcium phosphate and a mixture of sintered alpha-tricalcium phosphate and sintered beta-tricalcium phosphate.

In a further embodiment, the osteoconductive supporting bodies comprise apatite and tricalcium phosphate so-called biphasic calcium phosphate (BCP) or consist of apatite and tricalcium phosphate. Preferably, the osteoconductive supporting bodies comprise hydroxyapatite and beta-tricalcium phosphate or consist of hydroxyapatite and beta-tricalcium phosphate. The biphasic calcium phosphate can in particular have a ratio of hydroxyapatite (HA) to beta-tricalcium phosphate (β-TCP) of 80:20 to 20:80. For example, the biphasic calcium phosphate can consist of 60% hydroxyapatite (HA) and 40% beta-tricalcium phosphate (β-TCP). In particular, the biphasic calcium phosphate can consist of 50% hydroxyapatite (HA) and 50% beta-tricalcium phosphate (β-TCP). The greater the content of hydroxyapatite (HA), the more slow and controlled the breakdown (degradation) or resorption will be. By means of sintering, one can form compact, highly crystalline structures with crystallite sizes of a few μm. With respect to further features and advantages of the apatite and the tricalcium phosphate, the above description is incorporated herein by reference.

In a further embodiment, the supporting bodies have a roughened surface. This makes it possible to optimize growth or adhesion of bone tissue, in particular to an osteoconductive guide structure formed by the supporting bodies. The term "roughen" is to be understood within the meaning of the present invention as meaning in particular that roughness of the surface is increased after shaping of the supporting bodies, in particular in a production step provided for this purpose. The roughening can for example be carried out by etching, in particular by means of phosphoric acid. Preferably, the supporting bodies have a roughened surface the roughness of which is increased by at least 10% compared to a non-roughened supporting body surface. The term "roughness" is understood in particular to mean an unevenness of the surface of the supporting bodies.

In a further embodiment, the supporting bodies can be produced by means of an additive manufacturing method.

In a further embodiment, the supporting bodies comprise calcium phosphate cement or consist of calcium phosphate cement. In particular, the calcium phosphate cement can be a calcium phosphate cement that is subjected before complete hardening to pressure, preferably absolute pressure, of at least 2 bar. In this way, the porosity can be reduced in a particularly advantageous manner.

In a further embodiment, the osteoconductive supporting bodies are attached to one another by material bonding, in particular glued to one another.

In a further embodiment, the osteoconductive supporting bodies are coated with a bonding agent. The bonding agent is preferably a bonding agent that can be partially dissolved by heat or a solvent such as e.g. N-methylpyrrolidone (NMP) or acetone. By using such a bonding agent, it is possible to bond the osteoconductive supporting bodies to one another by heating and subsequent cooling or by adding a solvent. The bonding agent can e.g. be polylactide and/or poly(lactide-co-glycolide) (PLGA). Alternatively or in combination, the bonding agent can be a polysaccharide, or the bonding agent can comprise a polysaccharide. The polysaccharide can in particular be selected from the group consisting of starch, amylose, amylopectin, dextran, dextrin, cellulose, methyl cellulose, ethyl cellulose, hydroxymethyl cellulose, hydroxyethyl cellulose, propyl cellulose, hydroxypropyl cellulose, butyl cellulose, hydroxybutyl cellulose, hydroxyethylmethyl cellulose, hydroxypropylmethyl cellulose, carboxymethyl cellulose, carboxyethyl cellulose, alginic acid, alginates, chitin, chitosan, hyaluronic acid, dextran sulfate, heparin, heparan sulfate, chondroitin sulfates such as chondroitin 4-sulfate and/or chondroitin 6-sulfate, dermatan sulfate, keratan sulfate and mixtures thereof. Alternatively or in combination, the bonding agent can be a synthetic polymer, or the bonding agent can comprise a synthetic polymer. The synthetic polymer can in particular be selected from the group consisting of polyvinyl alcohol, polyethylene glycols, ethylene oxide-propylene oxide copolymers (EO-PO copolymers), ethylene oxide-propylene oxide block copolymers (EO-PO block copolymers), acrylic acid homopolymers, acrylic acid copolymers, polyvinylpyrrolidone homopolymers, polyvinylpyrrolidone copolymers and mixtures thereof.

In a further embodiment, the osteoconductive supporting bodies are configured such that they facilitate compaction, preferably impaction, in particular mutual clamping or wedging-in, of the supporting bodies, for example by means of a suitable instrument such as an impactor. With respect to correspondingly suitable configurations of the osteoconductive supporting bodies, the following explanations are incorporated herein by way of reference.

In a further embodiment, the osteoconductive supporting bodies are regularly formed, i.e. according to a further embodiment are in the form of molded bodies. The term "regularly formed" is to be understood within the meaning of the present invention as referring in particular to the forms described in the following.

The osteoconductive supporting bodies, in particular molded bodies, can in particular have a polygonal cross-section. For example, the osteoconductive supporting bodies, in particular molded bodies, can have a triangular, square-shaped, rectangular, pentagonal, hexagonal, heptagonal, octagonal, nonagonal, decagonal or star-shaped cross-section.

Moreover, the osteoconductive supporting bodies, in particular molded bodies, can have different cross-sections. With respect to possible cross-sections, the cross-sections mentioned in the preceding paragraph are incorporated herein by reference.

In a further embodiment, the osteoconductive supporting bodies, in particular molded bodies, are configured to be polyhedral, in particular cuboid, cube-shaped, tetrahedron-shaped, prism-shaped, pyramid-shaped, truncated pyramid-shaped or spatula-shaped.

Moreover, the osteoconductive supporting bodies, in particular molded bodies, can have differing polyhedral configurations. In other words, the osteoconductive supporting bodies, in particular molded bodies, can be in different polyhedral forms. With respect to possible polyhedral configurations, the previous paragraph is incorporated herein by reference.

In a further embodiment, the osteoconductive supporting bodies, in particular molded bodies, have a cornerless cross-section. For example, the structural elements can have an oval, in particular circular or elliptical, cross-section.

In a further embodiment, the osteoconductive supporting bodies, in particular molded bodies, are configured to be non-polyhedral, in particular ball-shaped, conical, truncated cone-shaped, ring-shaped, toroid-shaped, or circular-cylindrical shaped.

Moreover, the osteoconductive supporting bodies, in particular molded bodies, can have differing non-polyhedral configurations. In other words, the osteoconductive supporting bodies, in particular molded bodies, can be in different non-polyhedral forms. With respect to possible non-polyhedral configurations, the previous paragraph is incorporated herein by reference.

In a further embodiment, the osteoconductive supporting bodies, in particular molded bodies, are configured in the form of oligopods, i.e. are oligopod-shaped.

The oligopods can have legs with a conical, and in particular a rotationally symmetrical configuration. The legs can have a cone angle of 5° to 25°, in particular 7° to 15°.

Moreover, the oligopods can have legs with a length of 0.5 mm to 5 mm, in particular 1.5 mm to 2.5 mm.

Moreover, the oligopods can have legs with an average diameter of 0.2 mm to 3 mm, in particular 0.3 mm to 0.7 mm.

The oligopods can be selected from the group consisting of tripods, tetrapods, pentapods, hexapods, heptapods, octapods and mixtures of at least two of the aforementioned oligopods.

According to the invention, it is particularly preferable for the osteoconductive supporting bodies to have a tetrapod-shaped configuration. A tetrapod-shaped configuration allows particularly effective mutual engagement of the osteoconductive supporting bodies.

In a further embodiment, the osteoconductive supporting bodies, in particular molded bodies, comprise oblong structural elements. In particular, the osteoconductive supporting bodies, in particular molded bodies, can be composed of oblong structural elements.

The term "oblong structural elements" is to be understood within the meaning of the present invention as referring to structural elements with a length-width ratio or length-diameter ratio>(spelled out: greater than) 1.

Preferably, the osteoconductive supporting bodies, in particular molded bodies, have structural elements that are oblong and extend in rectilinear fashion. Preferably, the osteoconductive supporting bodies, in particular molded bodies, are composed of structural elements that are oblong and extend in rectilinear fashion.

The oblong structural elements preferably have a polyhedral, in particular cuboid, cube-shaped, prism-shaped, pyramid-shaped, truncated pyramid-shaped or spatula-shaped arrangement. In other words, the structural elements of each osteoconductive supporting body, in particular a molded body, preferably have a polyhedral, in particular cuboid, cube-shaped, prism-shaped, pyramid-shaped, truncated pyramid-shaped or spatula-shaped arrangement.

The oblong structural elements can have a length of 0.4 mm to 5 mm, in particular 0.8 mm to 4.5 mm, and preferably 1 mm to 4 mm.

Moreover, the oblong structural elements can have a width or a diameter of 0.4 mm to 5 mm, in particular 0.8 mm to 4.5 mm, and preferably 1 mm to 4 mm.

Moreover, the oblong structural elements can have a cornerless cross-section. For example, the structural elements can have an oval, in particular circular or elliptical, cross-section.

Alternatively, the structural elements can have a polygonal cross-section. For example, the structural elements can have a triangular, square-shaped, rectangular, pentagonal, hexagonal, heptagonal, octagonal, nonagonal, decagonal or star-shaped cross-section.

Osteoconductive supporting bodies, in particular in the form of molded bodies, with structural elements that are oblong and in particular extend in rectilinear fashion, in particular as described in the above embodiments, are advantageous in that by means of the mutual arrangement of the structural elements with respect to the supporting bodies, in particular molded bodies, additional hollow space volume can be created, allowing the osteoconductive properties of the supporting bodies, in particular molded bodies, and thus of the implant, to be additionally improved. In particular, this allows the pore size (absolute hollow space volume) and porosity (ratio of material volume to hollow space volume) of human or animal bone to be optimally reproduced.

In a further embodiment, the osteoconductive supporting bodies are irregularly formed.

The osteoconductive supporting bodies can in particular be in particulate form, i.e. in the form of particles.

In a further embodiment, the osteoconductive supporting bodies are configured as broken material.

In a further embodiment, the osteoconductive supporting bodies are configured as unbroken material. For example, the osteoconductive supporting bodies can be configured as an additively manufactured material, i.e. as a material that is produced by means of an additive manufacturing method.

Preferably, the osteoconductive supporting bodies are configured as bulk material, in particular as granules.

The term "bulk material" is to be understood within the meaning of the present invention as referring to a particulate material, i.e. a material in the form of particles having at least one measurement or dimension of less than 7 mm, preferably in a size range of 0.5 mm to 5 mm. The at least one measurement or dimension can in particular be the height and/or length and/or width (thickness) and/or the diameter, in particular the average diameter, of the particles. The term "granules" is to be understood within the meaning of the present invention as referring to a particulate material composed of irregularly formed, in particular broken and/or sieved, material.

Preferably, the osteoconductive supporting bodies have at least one measurement or dimension in a size range of 0.5 mm to 5 mm, in particular 0.1 mm to 3 mm, and preferably 1 mm to 2 mm. The at least one measurement or dimension can in particular be the height and/or width (thickness) and/or length and/or the diameter, in particular the average diameter, of the osteoconductive supporting bodies.

In a further embodiment, the osteoconductive supporting bodies are moveable with respect to one another, in particular displaceable with respect to one another.

In a further embodiment, the osteoconductive supporting bodies are configured to be impactable, i.e. mutually clampable or mutually wedgeable.

In a further embodiment, the osteoconductive supporting bodies are in impacted form, i.e. mutually clamped or mutually wedged.

In a further embodiment, the osteoconductive supporting bodies, preferably by means of impaction, can be converted into a three-dimensional structure or matrix, in particular comprising hollow and/or intermediate spaces, or are in the form of such a structure or matrix. Within the meaning of the present invention, such a structure or matrix can also be referred to as an osteoconductive guide structure or osteoconductive guide matrix.

The hollow or intermediate spaces of the structure or matrix can have a diameter, in particular an average diameter, of 0.1 mm to 1.2 mm, in particular 0.2 mm to 1 mm, and preferably 0.3 mm to 0.8 mm.

Moreover, in a particularly advantageous manner, the structure or matrix can have a hollow or intermediate space volume of 5% to 95%, in particular 10% to 80%, and preferably 20% to 70%. Such a hollow or intermediate space volume optimally reflects the pore volume of a human or animal spongiosa and provides an improvement in the osteoconductivity of the implant and in particular the biological reconstruction of a bony defect.

Moreover, the hollow or intermediate spaces of the structure or matrix are preferably at least partially connected to one another. In this way, the three-dimensional structure optimally reflects the porosity, in particular the interconnecting porosity, of the human or animal spongiosa. This also makes it possible, in a particularly advantageous manner, to stimulate and/or enhance the growth of bone tissue into a defective bone area, in particular the infiltration of vital bone tissue throughout a defective bone area. This also contributes to an improvement in the osteoconductive properties of the implant and in particular the biological reconstruction of a bone defect.

Moreover, the structure or matrix preferably has an elastic modulus, also referred to below as an E modulus, of 10 MPa to 10 GPa, in particular 50 MPa to 1 GPa, and preferably 80 MPa to 350 MPa. The term "elastic modulus (E modulus)" is to be understood within the meaning of the present invention as referring to the elastic modulus. The elastic modulus increases with increasing resistance of a material to its elastic deformation. A body composed of a material with a high elastic modulus is therefore stiffer than a body of the same configuration (the same geometric dimension) composed of a material with a low elastic modulus. The values for elastic modulus disclosed in this paragraph optimally reflect the corresponding values of spongy bone having an elastic modulus of 100 MPa to 1,000 MPa.

Due to the low E moduli described in the preceding paragraph, the osteoconductive supporting bodies can be uniformly, i.e. homogeneously, subjected to mechanical loading. In particular, the hollow or intermediate spaces of the structure or matrix described in the preceding paragraphs can be mechanically loaded. By means of uniform or homogenous mechanical loading of the osteoconductive supporting bodies and thus the implant, it is in turn possible in a particularly advantageous manner to achieve bone formation, in particular bone regeneration, within an entire bony defect area.

In a further advantageous embodiment from the standpoint of supporting or weight-bearing capacity, the osteoconductive supporting bodies have openings or recesses, in particular through openings. The openings or recesses can be selected from the group consisting of holes, pores, cracks, slits, chinks, gaps, notches and combinations of at least two of the aforementioned openings or recesses.

Such a configuration of the supporting bodies is advantageous in that the supporting bodies can (more easily) be compressed, in particular deformed, on loading. Corresponding loads leading to compression of the supporting bodies can arise for example on application of force by a user, preferably a surgeon. In this manner, compaction, in particular impaction, of the osteoconductive supporting bodies can be additionally improved, which in turn results in improved weight-bearing properties of the implant.

The openings or recesses can furthermore be geometrically defined or undefined openings or recesses.

In particular, the openings or recesses can have an oval, in particular circular or elliptical, cross-section. Alternatively or in combination, the openings or recesses can have a polygonal, in particular triangular, square-shaped, rectangular, pentagonal, hexagonal, heptagonal, octagonal, nonagonal, decagonal or star-shaped cross-section.

The openings or recesses can have a diameter of 0.01 mm to 5 mm, in particular 0.1 mm to 4 mm, and preferably 0.5 mm to 3 mm. Such diameters can be preferable when the openings are configured as through openings, through which a pulling element is to be guided, as explained in further detail below, in order to bond or secure the osteoconductive supporting bodies to one another.

In an alternative embodiment, the openings or recesses have a diameter, in particular an average diameter, of 60 μm to 500 μm, and preferably 100 μm to 400 μm. Such diameters are preferable when the openings or recesses are configured as pores.

Preferably, the openings or recesses are pores. In other words, the osteoconductive supporting bodies are preferably configured with open pores. In particular, the osteoconductive supporting bodies can show interconnecting porosity.

In a further embodiment, the osteoconductive supporting bodies comprise fibers. The fibers can generally be short and/or long fibers.

The term "short fibers" is to be understood within the meaning of the present invention as referring to fibers with a length of 0.01 mm to 1 mm, in particular 0.1 mm to 1 mm, and preferably 0.5 mm to 1 mm.

The term "long fibers" is to be understood within the meaning of the present invention as referring to fibers with a length>(spelled out: greater than) 1 mm.

The short or long fibers can be metal fibers and/or polymer fibers. With respect to possible metals and/or polymers from which the short or long fibers can be formed, the metals or polymers mentioned in the following in connection with the insertion aid are incorporated herein by reference.

In a further embodiment, the implant further comprises a pulling element. The pulling element is preferably configured to be guided via through openings of the osteoconductive supporting bodies. It is thus possible, in a particularly advantageous manner, to bond or secure the osteoconductive supporting bodies to one another. The pulling element is therefore preferably an oblong pulling element.

Preferably, the pulling element is a textile, in particular thread-shaped, pulling element. For example, the pulling element can be a thread (pulling thread), in particular a monofilament, pseudomonofilament or multifilament thread. In particular, the pulling element can be a surgical suture material.

Moreover, the pulling element can be a textile flat structure, in particular in the form of a knit fabric, braided fabric, crocheted fabric, laid fabric, web or nonwoven fabric. Preferably, the pulling element is a mesh, in particular a small-pore mesh, and preferably a hernia mesh. By incorporating the osteoconductive supporting bodies into a mesh-shaped pulling element, a regular arrangement of the supporting bodies can be obtained.

Alternatively, the pulling element can be a wire (pulling wire).

Further advantages that can be provided by using the pulling element are described below.

The use of a pulling element allows securing or fastening of the osteoconductive supporting bodies, by means of which an immediate increase in the mutual strength of the osteoconductive supporting bodies and thus of the implant can be achieved. In a particularly advantageous manner, this can mean that a smaller amount of the bone cement is required in order to obtain an implant capable of supporting or bearing weight. In addition, such an increase in the strength of the osteoconductive supporting bodies makes it possible to reduce the risk that a framework structure formed by the supporting bodies will fall apart following a brittle fracture. An open-pore framework structure can be obtained in a particularly advantageous manner by securing or fastening of the osteoconductive supporting bodies. Moreover, it is also possible for a pulling element-supporting body unit (or optionally a plurality of pulling element-supporting body units) to be fixed to a further implant and/or a bone and thus fastened in place in a locally stable manner. This fastening allows a pulling element-supporting body unit (or pulling element-supporting body units) to be pressed against a further implant, for example a freshened bone. This makes optimal binding to the bone possible, and the resulting pressure on the bone promotes bone growth. The implant preferably absorbs the transfer of force to the bone defect. This eliminates the pressure stimulus that results in bone remodeling (stress shielding). This pressure stimulus can be built up by the pulling element-supporting body units that are under pressure with respect to the bone.

The pulling element can comprise a material, in particular a polymer and/or a metal, or consist of a material, in particular a polymer and/or metal, as will be described in further detail below with respect to the insertion aid.

In a further embodiment, the osteoconductive supporting bodies are configured such that they are connectable to one another by positive bonding, non-positive bonding and/or material bonding. Preferably, the osteoconductive supporting bodies are configured such that they are connectable to one another by positive bonding. For example, the supporting bodies can be configured such that they can be connected to one another via a plug-in system or in the manner of a plug-in system. The plug-in system can be based on a so-called pin-hole principle, preferably with an undercut for better anchoring of the osteoconductive supporting bodies. For this purpose, part of the osteoconductive supporting bodies can be provided with pins, and another part of the osteoconductive supporting bodies can be provided with corresponding pinholes or slits.

In a further embodiment, the osteoconductive supporting bodies are connected to one another by positive bonding, non-positive bonding and/or material bonding. Preferably, the supporting bodies are connected to one another by positive bonding. For example, the osteoconductive supporting bodies can be connected to one another via a plug-in system or in the manner of a plug-in system. With respect to the plug-in system, the previous paragraph is incorporated herein by reference.

In a further embodiment, the supporting bodies are configured such that they are connectable to another implant by positive bonding, non-positive bonding and/or material bonding. Preferably, the supporting bodies are configured such that they are connectable to another implant by positive bonding. For example, the supporting bodies can be configured such that they can be connected to an implant via a plug-in system or in the manner of a plug-in system. The plug-in system can be based on a so-called pin-hole principle. For this purpose, the supporting bodies can be provided with a pin, and the other implant can have complementary pinholes or slits. The reverse situation is also possible according to the invention.

In a further embodiment, the osteoconductive supporting bodies are connected to one another via oblong connecting elements. Preferably, the connecting elements project for this purpose into recesses or openings in the supporting bodies. With respect to possible configurations of the recesses or openings in the supporting bodies, the above description is incorporated herein by reference. The connecting elements and the osteoconductive supporting bodies can comprise the same material or consist of the same material. However, it is preferable for the connecting elements and the osteoconductive supporting bodies to comprise different materials or consist of different materials.

The oblong connecting elements can comprise a material, in particular a polymer and/or a metal, or consist of a material, in particular a polymer and/or a metal, as will be described in further detail below with respect to the insertion aid.

In a further embodiment, the content of the osteoconductive supporting bodies is 10 wt % to 95 wt %, in particular 20 wt % to 90 wt %, and preferably 30 wt % to 70 wt %, based on the total weight of the implant.

In a further embodiment, the insertion aid is configured to be at least partially flexible or elastic. An insertion aid configured to be at least partially flexible or elastic is advantageous in that the insertion aid, for example by bending, can be more easily adapted to the contour of a bone. A further advantage is that an insertion aid configured to be at least partially flexible or elastic facilitates an application of pressure or force to the osteoconductive supporting bodies after insertion into a bony defect. This in turn facilitates compaction, in particular impaction, of the osteoconductive supporting bodies, preferably with formation of an osteoconductive guide structure, thus achieving sufficient secondary stability and in particular biological reconstruction of a bone defect to be treated.

The insertion aid can in particular be configured to be completely flexible or elastic.

In an alternative embodiment, the insertion aid is configured to be rigid.

In a further embodiment, the insertion aid is configured to be dimensionally unstable. A dimensionally unstable insertion aid is advantageous in that it facilitates adaptation of the implant to a bone defect to be treated. A preferred dimensionally unstable configuration of the insertion aid is in particular a mesh or bonding agent, which will be explained in further detail below.

In an alternative embodiment, the insertion aid is configured to be dimensionally stable. A preferred dimensionally stable configuration of the insertion aid is in particular a plate-shaped covering, which will be explained in further detail below.

In a further embodiment, the insertion aid comprises a material or consists of a material selected from the group consisting of proteins such as extracellular protein, polysaccharides such as mucopolysaccharides and/or cellulose derivatives, biological tissue, prepared or purified biological tissue, extracellular matrix, polycarbonates such as polytrimethylene carbonate, poly-para-dioxanone, polyhydroxyalkanoate, polyvinyl alcohol, polyethylene glycols, ethylene oxide-propylene oxide copolymers (EO-PO copolymers), ethylene oxide-propylene oxide block copolymers (EO-PO block copolymers), glycerol, polyolefin, polyester, polyamide, polyurethane, polyacrylic acids, acrylic acid homopolymers, acrylic acid copolymers, polyvinylpyrrolidone homopolymers, polyvinylpyrrolidone copolymers, elastomers such as thermoplastic elastomer, polyether ketone, organic polysulfide, metal, alloy and combinations, in particular mixtures or composite structures, of at least two of the aforementioned materials.

The protein can in particular be selected from the group consisting of collagen, gelatin, elastin, reticulin, fibronectin, fibrin, laminin, albumin and mixtures of at least two of the aforementioned proteins. The collagen is preferably collagen type I, collagen type III or a mixture comprising or consisting of collagen type I and collagen type III.

The polysaccharide can in particular be selected from the group consisting of starch, amylose, amylopectin, dextran, dextrin, cellulose, methyl cellulose, ethyl cellulose, hydroxymethyl cellulose, hydroxyethyl cellulose, propyl cellulose, hydroxypropyl cellulose, butyl cellulose, hydroxybutyl cellulose, hydroxyethyl methyl cellulose, hydroxypropyl methyl cellulose, carboxymethyl cellulose, carboxyethyl cellulose, alginic acid, alginates, chitin, chitosan, hyaluronic acid, dextran sulfate, heparin, heparan sulfate, chondroitin sulfates such as chondroitin 4-sulfate and/or chondroitin 6-sulfate, dermatan sulfate, keratan sulfate and mixtures of at least two of the aforementioned polysaccharides.

The biological tissue can in particular be an animal or xenogeneic, preferably bovine, equine or porcine, tissue.

The tissue can generally be selected from the group consisting of pericardium, peritoneum, small intestinal submucosa, gastric submucosa, bladder submucosa, uterine submucosa, serosa and mixtures of at least two of the aforementioned tissues.

Preferably, the tissue is selected from the group consisting of the pericardium (pericardial sac), pericardium fibrosum, pericardium serosum, epicardium, squamous epithelium, tunica serosa, muscle such as e.g. the myocardium and mixtures of at least two of the aforementioned tissues.

Particularly preferably, the tissue is pericardial tissue, in particular bovine pericardium, i.e. bovine pericardial tissue.

The prepared or purified biological tissue can in particular be a biological tissue freed of non-collagenous components, preferably fats and/or enzymes and/or non-collagenous proteins. Particularly preferably, the prepared or purified tissue is a collagen material produced from bovine pericardium, purified of non-collagenous components, in particular fats, enzymes and non-collagenous proteins, and freeze-dried. Such a material is already commercially distributed by the applicant under the brand name Lyoplant® for dural replacement. With respect to further features of the tissue, the above description is incorporated herein by reference.

The extracellular matrix can in particular be an extracellular matrix of a biological tissue. Preferably, the extracellular matrix is the extracellular matrix of an animal, in particular bovine, equine or porcine tissue. With respect to further features of the tissue, the above explanations are also incorporated herein by reference.

The polyhydroxyalkanoate can in particular be selected from the group consisting of polyglycolide, polylactide, polycaprolactone, poly-3-hydroxybutyrate, poly-4-hydroxybutyrate, copolymers of at least two of the aforementioned polymers and mixtures (blends) of at least two of the aforementioned polymers.

The polyolefin can in particular be selected from the group consisting of polyethylene (PE), low-density polyethylene, high-density polyethylene, high-molecular-weight polyethylene (HMWPE), ultra-high-molecular-weight polyethylene (UHMWPE), polypropylene (PP), polytetrafluoroethylene (PTFE), polyvinylidene fluoride, polyvinyl chloride, polytetrafluoropropylene, polyhexafluoropropylene, copolymers of at least two of the aforementioned polyolefins and mixtures (blends) of at least two of the aforementioned polyolefins.

The polyester can in particular be selected from the group consisting of polyethylene terephthalate, polypropylene terephthalate, polybutylene terephthalate, copolymers of at least two of the aforementioned polyesters and mixtures (blends) of at least two of the aforementioned polyesters.

The polyamide can in particular be selected from the group consisting of polyamide 6 (a polymer of ε-caprolactam or ω-aminocaproic acid units), polyamide 66 (a polymer of hexamethylenediamine and adipic acid units), polyamide 69 (a polymer of hexamethylenediamine and azelaic acid units), polyamide 612 (a polymer of hexamethylenediamine and dodecanedioic acid units), polyamide 11 (a polymer of 11-aminoundecanoic acid units), polyamide 12 (a polymer of laurolactam or ω-aminododecanoic units), polyamide 46 (a polymer of tetramethylenediamine and adipic acid units), polyamide 1212 (a polymer of dodecanediamine and dodecanedioic acid units), polyamide 6/12 (a polymer of caprolactam and laurolactam units), polyamide 66/610 (a polymer of hexamethylenediamine, adipic acid and sebacic acid units), copolymers of at least two of the aforementioned polyamides and mixtures (blends) of at least two of the aforementioned polyamides.

The thermoplastic elastomer can in particular be selected from the group consisting of thermoplastic copolyamide, thermoplastic polyester elastomer, thermoplastic copolyester, olefin-based thermoplastic elastomer, styrene block copolymer, urethane-based thermoplastic elastomer, olefin-based crosslinked thermoplastic elastomer, copolymers of at least two of the aforementioned elastomers and mixtures (blends) of at least two of the aforementioned elastomers.

The polyether ketone can in particular be selected from the group consisting of polyether ketone ketone, polyether ether ether ketone, polyether ether ketone ketone, polyether ketone ether ketone ketone, copolymers of at least two of the aforementioned polyether ketones and mixtures (blends) of at least two of the aforementioned polyether ketones.

The metal can in particular be selected from the group consisting of titanium and tantalum.

The alloy can in particular be selected from the group consisting of steel such as high-grade steel, stainless steel or high-alloy steels, in particular with chromium, nickel, duplex steels and mixtures thereof.

In a further embodiment, the insertion aid comprises a textile flat structure.

In a further embodiment, the insertion aid is configured as a textile flat structure.

Preferably, in the case of the two embodiments last described, the osteoconductive supporting bodies are fixed or fastened to the textile flat structure. Particularly preferably, the osteoconductive supporting bodies are fixed or fastened to the textile flat structure on only one side of the structure, in particular only on a side that faces the bone defect when inserted.

The textile flat structure can in particular be selected from the group consisting of tissue, knit fabrics, crocheted fabric, braided fabric, web, nonwoven fabric, mesh, felt and mesh fabric.

Moreover, the textile flat structure can comprise threads or be composed of threads selected from the group consisting of monofilaments, pseudomonofilaments, multifilaments and combinations of at least two of the aforementioned threads.

According to a particularly preferred embodiment, the textile flat structure is a mesh, in particular a knitted mesh. In other words, it is particularly preferable for the insertion aid to comprise a mesh, in particular a knitted mesh, or to be configured as a mesh, in particular a knitted mesh.

In a further embodiment, the textile flat structure, in particular threads thereof, comprises an additive, such as e.g. an active compound and/or an x-ray contrast agent. With respect to suitable additives, the additives explained in further detail below are incorporated herein by reference.

In general, threads of the textile flat structure can have the same thread thickness (thread diameter). From the standpoint of dimensional stability, however, it may be preferable for the textile flat structure to comprise threads with different thread thicknesses (thread diameters).

Moreover, the threads of the textile structure can be in dyed form, in particular at least partially dyed, for example dyed white and/or blue. The dyed threads can in particular be orientation threads, which facilitate proper placement of the insertion aid and in particular the implant for a user, preferably a surgeon.

In a further embodiment, the textile flat structure comprises a fastening device. The fastening device is preferably configured to allow fastening of the textile flat structure to or in a bone.

The fastening device can for example be configured as a hole, reinforced hole, eyelet, sleeve, slit, gap or loop.

The fastening device can furthermore be configured as a textile, in particular as a thread or thread loop.

In a particularly advantageous manner, the fastening device can be composed of a stiffer material than the textile flat structure.

In a further embodiment, the textile flat structure, in particular the mesh, is the product available from the applicant under the brand name Optilene® Mesh. This is a knitted mesh with monofilament polypropylene threads, a weight per unit area of 60 g/m² and a pore size of approx. 1.5 mm.

In a further embodiment, the textile flat structure, in particular the mesh, is the product available from the applicant under the brand name Optilene® Mesh LP. This is a knitted mesh with monofilament polypropylene threads, a weight per unit area of 36 g/m² and a pore size of approx. 1.0 mm.

In a further embodiment, the textile flat structure, in particular the mesh, is the product available from the applicant under the brand name Optilene® Mesh Elastic. This is a knitted mesh with monofilament polypropylene threads, a weight per unit area of approx. 48 g/m² and a pore size of approx. 3.6 mm×2.8 mm.

With respect to further suitable materials for the textile flat structure, in particular the mesh, the materials already described in connection with the insertion aid, in particular polymers, are incorporated herein by reference.

In a further embodiment, the insertion aid comprises a grid-shaped flat structure.

In a further embodiment, the insertion aid is configured as a grid-shaped flat structure.

Preferably, in the case of the two embodiments last described, the osteoconductive supporting bodies are fixed or fastened to the grid-shaped flat structure. Particularly preferably, the osteoconductive supporting bodies are fixed or fastened to the grid-shaped flat structure on only one side of said structure, in particular only on a side that faces the bone defect when inserted.

The grid-shaped flat structure preferably comprises a metal or consists of a metal. The metal can in particular be titanium and/or tantalum. Preferably, the grid-shaped flat structure is a metal grid, in particular composed of titanium and/or tantalum.

With respect to further suitable materials for the grid-shaped flat structure, the materials already described in connection with the insertion aid, in particular metals, are incorporated herein by reference.

In a further embodiment, the insertion aid comprises a bonding agent, in particular a hardened or solidified bonding agent. The use of a bonding agent is advantageous in that by means of gluing, uncontrolled dispersion of the osteoconductive supporting bodies on insertion into a bone defect to be treated can be prevented.

In a further embodiment, the insertion aid is configured as a bonding agent, in particular a hardened or solidified bonding agent.

Preferably, in the case of the two embodiments last described, osteoconductive supporting bodies are connected, in particular glued to one another by the bonding agent, preferably with formation of a kneadable or pasty mass or preparation. A kneadable or pasty consistency of a mass or preparation produced by the bonding agent and the osteoconductive supporting bodies allows in a particularly advantageous manner an intraoperative change in the form and/or amount thereof. This in turn facilitates the adaptation of the implant to a bone defect to be treated and thus improves the handling of the implant.

In a further embodiment, the bonding agent comprises a protein such as extracellular protein or consists of a protein such as extracellular protein. The protein is preferably selected from the group consisting of collagen, gelatin, elastin, laminin, reticulin, fibronectin, fibrin, albumin and mixtures of at least two of the aforementioned proteins. With respect to further suitable proteins, the proteins already described in connection with the insertion aid are incorporated herein by reference.

In a further embodiment, the bonding agent comprises a polysaccharide such as a cellulose derivative and/or mucopolysaccharide. The polysaccharide is preferably selected from the group consisting of starch, amylose, amylopectin, dextran, dextrin, cellulose, methyl cellulose, ethyl cellulose, hydroxymethyl cellulose, hydroxyethyl cellulose, propyl cellulose, hydroxypropyl cellulose, butyl cellulose, hydroxybutyl cellulose, hydroxyethylmethyl cellulose, hydroxypropylmethyl cellulose, carboxymethyl cellulose, carboxyethyl cellulose, alginic acid, alginates, chitin, chitosan, hyaluronic acid, dextran sulfate, heparin, heparan sulfate, chondroitin sulfates such as chondroitin 4-sulfate and/or chondroitin 6-sulfate, dermatan sulfate, keratan sulfate and mixtures of at least two of the aforementioned polysaccharides.

In a further embodiment, the bonding agent comprises a synthetic polymer. The synthetic polymer is preferably selected from the group consisting of polyvinyl alcohol, polyethylene glycols, ethylene oxide-propylene oxide copolymers (EO-PO copolymers), ethylene oxide-propylene oxide block copolymers (EO-PO block copolymers), acrylic acid homopolymers, acrylic acid copolymers, polyvinylpyrrolidone homopolymers, polyvinylpyrrolidone copolymers and mixtures thereof.

In a further embodiment, the bonding agent comprises a mixture of a protein and a polysaccharide, a mixture of a protein and a synthetic polymer, a mixture of a polysaccharide and a synthetic polymer or a mixture of a protein, a polysaccharide and a synthetic polymer. With respect to suitable proteins, suitable polysaccharides and suitable synthetic polymers, the preceding paragraphs are incorporated herein by reference.

In a further embodiment, the bonding agent comprises a diluent. The diluent is preferably glycerol. A diluent-containing bonding agent is advantageous in that a preferably pasty or kneadable consistency of the bonding agent can be maintained until completion of a bone defect treatment. This facilitates adaptation of the implant to the form of a bone defect to be treated.

In a further embodiment, the bonding agent comprises an amount of a liquid diluent, preferably glycerol and/or water, of 50 wt % to 95 wt %, in particular 60 wt % to 90 wt %, and preferably 70 wt % to 80 wt %, based on the total weight of the bonding agent. The diluent contents given in this paragraph are particularly advantageous with respect to maintenance of a preferably pasty or kneadable consistency of the bonding agent until completion of a bone defect treatment.

In a further embodiment, the bonding agent is an anhydrous bonding agent or an essentially anhydrous bonding agent. The term "essentially anhydrous bonding agent" is to be understood within the meaning of the present invention as referring to a bonding agent that has a water content of less than 5 wt %, in particular less than 3 wt %, and preferably less than 1 wt %, based on the total weight of the bonding agent. Preferably, the bonding agent is an anhydrous bonding agent or an essentially anhydrous bonding agent comprising carboxymethyl cellulose and glycerol. This allows a dough-like consistency to be achieved, which provides adhesive properties and thus allows favorable prefixing in a bone defect to be treated.

In a further embodiment, the bonding agent has a dissolution time in a human or animal (non-human) body of 30 min to 144 hours, in particular 30 min to 72 hours, and preferably 30 min to 24 hours. In this manner, one can achieve rapid growth of bone tissue into a bone defect in a particularly advantageous manner.

In a preferred embodiment, the bonding agent is configured as an adhesive. The adhesive preferably comprises an oligopeptide, in particular with 2 to 100 amino acid units, and/or a nitrogen-functionalized polysaccharide and/or a terminal oligolactam. An adhesive with a nitrogen-functionalized polysaccharide and a terminal oligolactam is known from EP 2185207 B1, the disclosed content of which is incorporated into the content of the present description by reference in its entirety. Moreover, the adhesive can be configured in particular as a reactive adhesive, in particular with at least two components, or as a finished hot-melt adhesive.

In a further embodiment, the insertion aid comprises a textile flat structure, preferably a mesh, and a bonding agent.

In a further embodiment, the insertion aid is configured as a combination, in particular a composite, of a textile flat structure, preferably a mesh, and a bonding agent.

Preferably, in the case of the two embodiments last described, the osteoconductive supporting bodies are fixed by means of the bonding agent to the textile flat structure, preferably a mesh, or are bonded, in particular glued, to the textile flat structure, preferably a mesh. Particularly preferably, the osteoconductive supporting bodies are fixed or bonded, in particular glued, to the textile flat structure, preferably a mesh, by the bonding agent on only one side, in particular only on a side that faces the bone defect when inserted, of said textile flat structure, preferably a mesh. With respect to further features and advantages of the textile flat structure, in particular the mesh, and the bonding agent, the above description is incorporated herein by reference in its entirety.

In a further embodiment, the insertion aid comprises a grid-shaped flat structure, preferably a metal grid, and a bonding agent.

In a further embodiment, the insertion aid is configured as a combination, in particular a composite, of a grid-shaped flat structure, preferably a metal grid, and a bonding agent.

Preferably, in the case of the two embodiments last described, the osteoconductive supporting bodies are fixed by means of the bonding agent to the grid-shaped flat structure, preferably a metal grid, or are bonded, in particular glued, to the grid-shaped flat structure, preferably a metal grid. Particularly preferably, the osteoconductive supporting bodies are fixed or bonded, in particular glued, to the grid-shaped flat structure, preferably a metal grid, by the bonding agent on only one side, in particular only on a side that faces the bone defect when inserted, of said structure or grid. With respect to further features and advantages of the grid-shaped flat structure, in particular a metal grid, and the bonding agent, the above description is incorporated herein by reference in its entirety.

In a further embodiment, the insertion aid comprises a textile flat structure, preferably a mesh, a grid-shaped flat structure, preferably a metal grid, and a bonding agent.

In a further embodiment, the insertion aid is configured as a combination, in particular a composite, of a textile flat structure, preferably a mesh, a grid-shaped flat structure, preferably a metal grid, and a bonding agent.

Preferably, in the case of the two embodiments last described, the osteoconductive supporting bodies are fixed by means of the bonding agent to the textile flat structure, preferably a mesh, and/or the grid-shaped flat structure, preferably a metal grid, or are bonded, in particular glued, to the textile flat structure, preferably a mesh, and/or the grid-shaped flat structure, preferably a metal grid. Particularly preferably, the osteoconductive supporting bodies are fixed or bonded, in particular glued, to the textile flat structure, preferably a mesh, and/or the grid-shaped flat structure, preferably a metal grid, by the bonding agent on only one side, in particular only on a side that faces the bone defect when inserted, of said structure(s). With respect to further features and advantages of the textile flat structure, preferably a mesh, the grid-shaped flat structure, in particular a metal grid, and the bonding agent, the above description is incorporated herein by reference in its entirety.

In a further embodiment, the insertion aid comprises a sheath enclosing or surrounding the supporting bodies.

In a further embodiment, the insertion aid is configured as a sheath enclosing or surrounding the supporting bodies.

The use of a sheath is advantageous in that uncontrolled migration of the osteoconductive supporting bodies on insertion into a bone defect to be treated can be prevented.

In general, the sheath can have a dimensionally unstable, in particular a bag-shaped configuration.

Alternatively, the sheath can be dimensionally stable, in particular preformed. For example, the sheath can have a vessel-shaped, recipient-shaped, or container-shaped configuration. Preferably, the sheath has a shape that is anatomically adapted, i.e. adapted to a bone defect to be treated.

Preferably, the sheath has a pillow-shaped, sack or pouch-shaped, wedge-shaped, apple slice-shaped, sickle-shaped, sickle wedge-shaped, ring-shaped, toroid-shaped or cloverleaf-shaped configuration.

In a further embodiment, the sheath is configured to be closeable, in particular by means of a thread, preferably a pulling or securing thread. Alternatively, the sheath can have a Velcro fastener.

In a further embodiment, the sheath comprises openings or recesses. The openings or recesses can be selected from the group consisting of holes, pores, cracks, slits, chinks, gaps, notches and combinations of at least two of the aforementioned openings or recesses. Preferably, the openings or recesses are pores.

In a preferred embodiment, the sheath is configured with open pores.

Preferably, the sheath comprises openings, in particular pores, with a diameter, preferably an average diameter, of 10 µm to 5 mm, in particular 100 µm to 3 mm, and preferably 500 µm to 2 mm. Such opening diameters, in particular pore diameters, have been found to be particularly advantageous for the growing in of bone tissue. Preferably, the openings of the sheath are smaller than a minimum dimension of the supporting bodies.

In a further embodiment, the sheath comprises a non-textile structure. In particular, the sheath can have a non-textile configuration, i.e. can be in the form of a non-textile structure.

The sheath comprises in a further embodiment a randomized fiber structure, i.e. a structure with randomly arranged and/or oriented fibers, or consists of such a structure.

In a further embodiment, the sheath is in lyophilized, i.e. freeze-dried form.

In a further embodiment, the sheath is configured to be grid-shaped, i.e. in the form of a grid, in particular a metal grid. With respect to suitable metals, the metals or alloys already described in connection with the insertion aid are incorporated herein by reference, wherein titanium and/or tantalum is/are preferred.

In a further embodiment, the sheath comprises a textile structure. According to the invention, it can in particular be preferable for the sheath to be configured in textile form, i.e. in the form of a textile structure.

The textile structure can comprise threads or consist of threads selected from the group consisting of monofilaments, pseudomonofilaments, multifilaments and combinations of at least two of the aforementioned threads.

The textile structure, in particular the threads thereof, can comprise an additive, such as e.g. an active compound and/or an x-ray contrast agent. With respect to suitable additives, the additives described below are incorporated herein by reference.

In general, threads of the textile flat structure can have the same thread thickness (thread diameter).

From the standpoint of dimensional stability, however, it may be preferable for the sheath, in particular the textile flat structure, to comprise threads with different thread thicknesses (thread diameters).

Moreover, threads of the textile structure can be in dyed form, in particular at least partially dyed, for example dyed white and/or blue. The dyed threads can in particular be orientation threads, which facilitate proper placement of the sheath and in particular the implant for a user, preferably a surgeon.

Moreover, the textile structure can be selected from the group consisting of tissue, knit fabrics, crocheted fabric, braided fabric, web, nonwoven fabric, mesh, felt and mesh fabric.

According to the invention, it can therefore be preferable for the sheath to have a woven, knitted, crocheted, braided, web-type, non-woven fabric-type, mesh-type, felt-type or mesh fabric type structure or to be composed of such a structure.

According to a particularly preferred embodiment, the configuration of the sheath is of the mesh type, i.e. in the form of a mesh, in particular a knitted mesh.

The mesh can e.g. be one of the products mentioned above distributed by the applicant under the brand names Optilene® Mesh, Optilene® Mesh LP and Optilene® Mesh Elastic.

In a further embodiment, the sheath comprises a shrinkable thread, i.e. a so-called shrink thread. Preferably, the shrink thread is configured to bring about by shrinking a change in shape, in particular a shape adaptation, of the sheath to a bone defect to be treated and/or a closure of the sheath. Shrinking of the thread can be brought about for example by irradiation and fixation. The shrink thread can for example comprise poly-4-hydroxybutyrate or consist of poly-4-hydroxybutyrate.

In a further embodiment, the sheath has a multilayer, in particular double-layer configuration. In other words, the sheath comprises according to a further embodiment a plurality of layers, in particular two layers.

The layers can be configured to be the same or different. In particular, the layers can comprise the same material or consist of the same material. Alternatively, the layers can consist of one or a plurality of different materials. With respect to suitable materials, the materials described in connection with the insertion aid are incorporated herein by reference in their entirety.

Moreover, each of the layers can be configured in textile form or non-textile form.

Moreover, the sheath can comprise at least one textile-form layer and at least one non-textile-form layer.

The layers are preferably arranged on top of one another and connected to one another, in particular connected to one another at the edges.

Bonding of the layers can be based on a seam, in particular a seam running along the edge of the layers, or on a material bond, in particular a material bond running along the edge of the layers, such as e.g. a glued or welded bond.

In a further embodiment, the sheath is only partially filled with the osteoconductive supporting bodies.

The sheath can in particular be filled to at most 90%, in particular at most 85%, and preferably at most 70% with the osteoconductive supporting bodies. The sheath is further preferably filled to at least 5%, and preferably at least 10% with the osteoconductive supporting bodies. This ensures in a particularly advantageous manner moldable and nonetheless stable filling of a bony defect.

In a further embodiment, the content of the sheath is 0.5 wt % to 50 wt %, in particular 5 wt % to 40 wt %, and preferably 2 wt % to 50 wt %, based on the total weight of the implant.

With respect to suitable materials for the sheath, the materials already described in connection with the insertion aid are incorporated herein by reference.

In a further embodiment, the implant comprises a plurality of insertion aids that are respectively configured as sheaths. Here, each sheath or only some of the sheaths may comprise the osteoconductive supporting bodies. In particular, only one of the sheaths may comprise the osteoconductive supporting bodies. In a particularly advantageous manner, this sheath can serve as a kind of "reservoir sheath" for filling the other (empty) sheaths.

Moreover, the sheaths can be of different sizes. In particular, one or a plurality of smaller sheaths may be contained in a larger sheath. The smaller sheath or sheaths and/or the larger sheath can comprise an in vivo degradable or in vivo resorbable material or consist of such a material. With respect to suitable materials, the materials described in connection with the insertion aid are incorporated herein by reference.

In a further embodiment, adjacent sheaths are separated from one another by an intermediate area of the implant. The intermediate area preferably comprises a textile structure. Alternatively, however, the intermediate area can also comprise a non-textile structure. With respect to suitable textile or non-textile structures, the corresponding descriptions given in connection with the sheath are incorporated herein by reference.

With respect to further features and advantages of the sheaths, the descriptions given in the preceding paragraphs, which apply mutatis mutandis, are incorporated herein by reference.

In a further embodiment, the insertion aid comprises a sheath enclosing or surrounding the supporting bodies and a bonding agent.

In a further embodiment, the insertion aid is configured as a combination, in particular a composite, of a sheath enclosing or surrounding the osteoconductive supporting bodies and a bonding agent.

Preferably, in the case of the last two embodiments described, the osteoconductive supporting bodies are fixed or connected, in particular glued, by the bonding agent to the sheath. With respect to further features and advantages of the sheath and of the bonding agent, the above description is incorporated herein by reference in its entirety.

In a further embodiment, the insertion aid comprises a covering.

In a further embodiment, the insertion aid is configured as a covering.

The covering is preferably configured to bring about complete closure of a bone defect. In a particularly advantageous manner, the covering can also provide support with respect to forces that act in vivo on a preferably artificial joint socket, on the bone, which makes it possible to achieve greater stability overall.

The term "complete closure" is to be understood within the meaning of the present invention as meaning that a bone defect is closed only incompletely by an artificial joint socket and the covering covers the bone defect in a remaining area.

In a particularly preferred embodiment, the covering is a plate-shaped covering. In other words, it is particularly preferable for the covering to be plate-shaped, i.e. configured as a plate.

The covering is configured in a further embodiment to be curved or bent. Preferably, the covering has a concave surface and/or a convex surface, preferably a concave surface and a convex surface, particularly preferably a concave surface and an opposite convex surface. The concave surface can in particular be a surface of the covering that faces the bone defect when implanted. Moreover, the convex surface can in particular be a surface of the covering that faces away from the bone defect when implanted. Moreover, the surface described in this paragraph or the surfaces described in this paragraph can in particular be a partial surface or partial surfaces of the covering.

In a further embodiment, the covering is configured in the form of a straight, i.e. not curved or not bent, plate.

In a preferred embodiment, the osteoconductive supporting bodies are fixed or fastened to the covering.

In a further embodiment, the osteoconductive supporting bodies are fixed or fastened to the covering on only one side thereof, in particular only on a side that faces the bone defect when inserted.

According to a particularly preferred embodiment, the osteoconductive supporting bodies are fixed or fastened to a curved, preferably concave surface, in particular a partial surface, of the covering. In particular, the osteoconductive supporting bodies can be fixed or fastened to the surface, in particular the partial surface, by means of a textile flat structure such as a mesh and/or a grid-shaped flat structure such as a metal grid and/or a sheath and/or a bonding agent, as described in further detail below. The surface, in particular the partial surface of the covering, can in particular be a surface that faces the bone defect when implanted, in particular a partial surface that faces the bone defect when implanted.

In a further embodiment, the covering comprises a connecting area. The connecting area is preferably configured as a connection to an artificial joint socket, in particular to an outer surface of an artificial joint socket.

The connecting area is preferably configured to correspond to an artificial joint socket, in particular to an outer surface of an artificial joint socket.

Particularly preferably, the connecting area is configured as a curved, preferably concave surface, in particular a partial surface, of the covering. The surface, in particular a partial surface, can in particular be a surface of the covering that faces the bone defect when implanted, in particular a partial surface that faces the bone defect when implanted.

In a further embodiment, the covering is configured as a single part.

In a further embodiment, the covering is configured in multiple parts, for example two or three parts. The parts of the covering are preferably connected to one another by material bonding, in particular glued or welded to one another. For example, the parts of the covering can be connected to one another by means of a polymethyl methacrylate adhesive (PMMA adhesive).

The term "polymethyl methacrylate adhesive" is to be understood within the meaning of the present invention as referring to an adhesive, in particular a two-component adhesive, which after hardening is in the form of polymethyl methacrylate or comprises polymethyl methacrylate.

In a further embodiment, the covering comprises at least one anchoring pin. The at least one anchoring pin is preferably configured for fastening or anchoring of the covering to or in a bone.

The term "at least one anchoring pin" is to be understood within the meaning of the present invention as referring to one anchoring pin or a plurality of anchoring pins, i.e. two or more anchoring pins.

The at least one anchoring pin can in particular be selected from the group consisting of at least one thorn-shaped anchoring pin, at least one spike-shaped anchoring pin, at least one nail-shaped anchoring pin, at least one screw-shaped anchoring pin, at least one hook-shaped anchoring pin, at least one prong-shaped anchoring pin, at least one barb-shaped anchoring pin, at least one sword-shaped anchoring pin, at least one arrow-shaped anchoring pin and combinations thereof.

In a preferred embodiment, the covering comprises a plurality of anchoring pins. The anchoring pins are preferably provided for fastening or anchoring of the covering to or in a bone.

The anchoring pins can in particular be selected from the group consisting of thorn-shaped anchoring pins, spike-shaped anchoring pins, nail-shaped anchoring pins, screw-shaped anchoring pins, hook-shaped anchoring pins, prong-shaped anchoring pins, barb-shaped anchoring pins, sword-shaped anchoring pins, arrow-shaped anchoring pins and combinations of at least two of the aforementioned anchoring pins.

In a further embodiment, the covering comprises at least one fastening means opening.

The term "at least one fastening means opening" is to be understood within the meaning of the present invention as referring to one fastening means opening or a plurality of fastening means openings, i.e. two or more fastening means openings.

The at least one fastening means opening is configured to accommodate a fastening means, such as e.g. a bone screw, in particular in the form of a locking screw or a bone nail. In a particularly advantageous manner, this provides an (additional) possibility for fastening or anchoring the covering to or in a bone.

The at least one fastening means opening can have an oval, in particular a circular or elliptical, cross-section. Alternatively, the at least one fastening means opening can have a polygonal, in particular a triangular, rectangular, square-shaped, pentagonal, hexagonal, heptagonal, octagonal, nonagonal, decagonal or star-shaped cross-section.

If the covering comprises a plurality of fastening means openings, the embodiments described in connection with the at least one fastening means opening apply mutatis mutandis.

In a further embodiment, the covering comprises at least one blood filling opening. The at least one blood filling opening is preferably configured to fill a space shielded by the covering and an optionally present artificial joint socket with blood or another fluid. The blood filling opening can also be used to flush out a bonding agent.

Within the meaning of the present invention, the term "at least one blood filling opening" refers to one blood filling opening or a plurality of blood filling openings, i.e. two or more blood filling openings.

In general, the at least one blood filling opening can have an oval, in particular circular or elliptical, cross-section.

Alternatively, the at least one blood filling opening can have a polygonal, in particular a triangular, rectangular, square-shaped, pentagonal, hexagonal, heptagonal, octagonal, nonagonal, decagonal or star-shaped cross-section.

In particular, the at least one blood filling opening can have a diameter that is smaller than a minimum dimension of the supporting bodies.

If the covering comprises a plurality of blood filling openings, the embodiments described in connection with the at least one blood filling opening apply mutatis mutandis.

In a further embodiment, the covering comprises weakened areas, in particular locally limited weakened areas.

The weakened areas are preferably selected from the group consisting of openings such as slits and/or slots, recesses such as grooves and/or notches, perforations, changes in thickness such as decreases in thickness, and combinations of at least two of the aforementioned weakened areas.

Weakened areas are advantageous in that they can facilitate adaptation of the covering to a bone defect, in particular to the contour of the surrounding bone. Weakened areas in the form of openings have the additional advantage of allowing a certain degree of "breathing" or "pumping" of the covering.

In a further embodiment, the covering is configured with open pores. In a particularly advantageous manner, this allows surrounding bone tissue to grow into the covering, which makes it possible to achieve sufficient secondary stability and in particular the biological reconstruction of a bone defect to be treated. Preferably, the covering is configured with open pores only in certain sections.

In a further embodiment, the covering is not configured to be porous. A covering that is not configured to be porous is advantageous in that in the case of removal of the covering, in particular during hip revision surgery, significantly less or no (newly formed) bone tissue has to be removed. Preferably, the covering is not configured to be porous only in certain sections.

In a further embodiment, the covering is configured to be smooth, i.e. without uneven areas. A smooth covering is also advantageous in that in the case of removal of the covering, in particular during hip revision surgery, significantly less or no (newly formed) bone tissue has to be removed. Preferably, the covering is configured to be smooth only in certain sections.

In a further embodiment, the covering is configured with open pores only along sections facing the bone defect when implanted, while the covering along sections facing away from the bone defect when implanted is smooth and/or not configured to be porous. This allows the advantages described in the above paragraphs to be combined with one another.

In a further embodiment, the covering comprises a ledge. In a particularly advantageous manner, this allows a large amount of osteoconductive supporting bodies to be inserted into a bone defect to be treated.

In a further embodiment, the covering comprises a connecting device for connecting the covering to a negative pressure or vacuum source, in particular a negative pressure or vacuum pump. In this manner, it is possible for example to clean a bone defect to be treated, in particular to remove loose bone particles and/or bodily fluids, such as e.g. blood.

In a further embodiment, the covering comprises a metal, in particular titanium and/or tantalum, or consists of a metal, in particular titanium and/or tantalum.

In a further embodiment, the covering comprises a polymer or consists of a polymer, wherein the polymer is preferably selected from the group consisting of polylactide, poly-3-hydroxybutyrate, poly-4-hydroxybutyrate, polyether ether ketone (PEEK) and mixtures (blends) of at least two of the aforementioned polymers.

In general, the covering can be in various forms depending on the respective bone defect to be treated.

In a further embodiment, the covering is produced by means of an additive or generative manufacturing method.

The term "additive manufacturing method" or "generative manufacturing method" is to be understood within the meaning of the present invention as referring to methods for the rapid and inexpensive manufacturing of models, patterns, samples, prototypes, tools, and final products ("additive manufacturing"). The manufacturing is carried out directly based on computer-internal data models of formless (fluids, powder or the like) or form-neutral (band or wire-shaped) material by means of chemical and/or physical processes.

In a further embodiment, the insertion aid comprises a bonding agent and a covering.

In a further embodiment, the insertion aid is configured as a combination, in particular a composite, of a bonding agent and a covering.

Preferably, in the case of the two embodiments last described, the osteoconductive supporting bodies are fixed or fastened, in particular glued to one another, by the bonding agent, and fixed or fastened to the covering, preferably to a curved, preferably concave, surface, in particular a partial surface, of the covering. The surface, in particular a partial surface, can in particular be a surface that faces the bone defect when implanted, in particular a partial surface of the covering that faces the bone defect when implanted. With respect to further features and advantages of the bonding agent and the covering, the above description is incorporated herein by reference in its entirety.

In a further embodiment, the insertion aid comprises a textile flat structure, preferably a mesh, and a covering.

In a further embodiment, the insertion aid is configured as a combination, in particular a composite, of a textile flat structure, preferably a mesh, and a covering.

Preferably, in the case of the two embodiments last described, the osteoconductive supporting bodies are fixed or fastened by the textile flat structure, preferably a mesh, to the covering, preferably to a curved, preferably concave, surface, in particular a partial surface of said covering. For this purpose, the textile flat structure, preferably a mesh, can in particular be fixed by material bonding to the covering or the surface, in particular a partial surface, for example by gluing or welding. The surface, in particular a partial surface, can in particular be a surface of the covering that faces the bone defect when implanted, in particular a partial surface that faces the bone defect when implanted. With respect to further features and advantages of the textile flat structure, preferably a mesh, and the covering, the above description is incorporated herein by reference in its entirety.

In a further embodiment, the insertion aid comprises a textile flat structure, preferably a mesh, a bonding agent and a covering.

In a further embodiment, the insertion aid is configured as a combination, in particular a composite, of a textile flat structure, preferably a mesh, a bonding agent and a covering.

Preferably, in the case of the two embodiments last described, the osteoconductive supporting bodies are connected, in particular glued to one another, and fixed or fastened by the bonding agent and/or the textile flat structure, preferably a mesh, to the covering, preferably to a curved, preferably concave, surface, in particular a partial surface of the covering. For this purpose, the textile flat structure, preferably a mesh, can in particular be fixed in a materially bonding manner to the covering or the surface, in particular a partial surface, for example by gluing or welding. The surface, in particular a partial surface, can in particular be a surface of the covering that faces the bone defect when implanted, in particular a partial surface that faces the bone defect when implanted. With respect to further features and advantages of the textile flat structure, preferably a mesh, of the bonding agent and the covering, the above description is incorporated herein by reference in its entirety.

In a further embodiment, the insertion aid comprises a grid-shaped flat structure, preferably a metal grid, and a covering.

In a further embodiment, the insertion aid is configured as a combination, in particular a composite, of a grid-shaped flat structure, preferably a metal grid, and a covering.

Preferably, in the case of the two embodiments last described, the osteoconductive supporting bodies are fixed or fastened by the grid-shaped flat structure, preferably a metal grid, to the covering, preferably to a curved, preferably concave, surface, in particular a partial surface, of the covering. For this purpose, the grid-shaped flat structure, preferably a metal grid, can in particular be fixed by material bonding to the covering or the surface, in particular a partial surface, for example by gluing or welding. The surface, in particular a partial surface, can in particular be a surface of the covering that faces the bone defect when implanted, in particular a partial surface that faces the bone defect when implanted. With respect to further features and advantages of the grid-shaped flat structure, preferably a metal grid, and the covering, the above description is incorporated herein by reference in its entirety.

In a further embodiment, the insertion aid comprises a grid-shaped flat structure, preferably a metal grid, a bonding agent and a covering.

In a further embodiment, the insertion aid is configured as a combination, in particular a composite, of a grid-shaped flat structure, preferably a metal grid, a bonding agent and a covering.

Preferably, in the case of the two embodiments last described, the osteoconductive supporting bodies are connected, in particular glued to one another, by the bonding agent, and fixed or fastened by the bonding agent and/or the grid-shaped flat structure, preferably a metal grid, to the covering, preferably to a curved, preferably concave, surface of the covering, in particular a partial surface. For this purpose, the grid-shaped flat structure, preferably a metal grid, can in particular be fixed by material bonding to the covering or the surface, in particular a partial surface, for example by gluing or welding. The surface, in particular a partial surface, can in particular be a surface of the covering that faces the bone defect when implanted, in particular a partial surface that faces the bone defect when implanted. With respect to further features and advantages of the grid-shaped flat structure, preferably a metal grid, of the bonding agent and the covering, the above description is incorporated herein by reference in its entirety.

In a further embodiment, the insertion aid comprises a sheath enclosing or surrounding the osteoconductive supporting bodies and a covering.

In a further embodiment, the insertion aid is configured as a combination, in particular a composite, of a sheath surrounding or enclosing the osteoconductive supporting bodies and a covering.

Preferably, in the case of the two embodiments last described, the osteoconductive supporting bodies are contained in the sheath, wherein the sheath is fixed or fastened to the covering, preferably to a curved, preferably concave, surface, in particular a partial surface, of the covering. For this purpose, the sheath can in particular be fixed by material bonding to the covering or the surface, in particular a partial surface, for example by gluing or welding. The surface, in particular a partial surface, can in particular be a surface of the covering that faces the bone defect when implanted, in particular a partial surface that faces the bone defect when implanted. With respect to further features and advantages of the sheath and the covering, the above description is incorporated herein by reference in its entirety.

In a further embodiment, the insertion aid comprises a sheath enclosing or surrounding the osteoconductive supporting bodies, a bonding agent and a covering.

In a further embodiment, the insertion aid is configured as a combination, in particular a composite, of a sheath enclosing or surrounding the osteoconductive supporting bodies, a bonding agent and a covering.

Preferably, in the case of the two embodiments last described, the osteoconductive supporting bodies are contained in the sheath. Further preferably, the osteoconductive supporting bodies are connected, in particular glued to one another, by the bonding agent, and fixed or fastened by the bonding agent and/or the sheath to a curved, preferably concave, surface of the covering, in particular a partial surface. For this purpose, the sheath can in particular be fixed by material bonding to the covering or the surface, in particular a partial surface, for example by gluing or welding. The surface, in particular a partial surface, can in particular be a surface of the covering that faces the bone defect when implanted, in particular a partial surface that faces the bone defect when implanted. With respect to further features and advantages of the sheath, the bonding agent and the covering, the above description is incorporated herein by reference in its entirety.

In a further embodiment, the implant further comprises an artificial joint socket. The artificial joint socket is preferably fixed or fastened to a covering of the insertion aid or to an insertion aid configured as a covering. Preferably, the artificial joint socket is fixed or fastened to a connecting area of the covering. The fixation or fastening is preferably based on a material bond, in particular adhesive bonding, for example by means of a PMMA adhesive. With respect to further features and advantages of the covering and the connecting areas of the covering, the above description is incorporated herein by reference in its entirety.

In a further embodiment, the implant further comprises a fastening device. The fastening device is preferably configured to carry out fastening of the implant to or in a bone.

The fastening device can for example be configured as a hole, reinforced hole, eyelet, sleeve, slit, gap or loop.

The fastening device can furthermore be configured as a textile, in particular as a thread or thread loop.

In a particularly advantageous manner, the fastening device can be composed of a stiffer material than the textile flat structure.

In a further embodiment, the implant further comprises a reinforcing structure (armoring structure). The reinforcing structure is preferably configured to provide armoring, i.e. reinforcement or strengthening, of the implant.

The reinforcing structure can for example comprise a textile structure or consist of such a structure.

Preferably, the reinforcing structure is configured in the form of a mesh, in particular in the form of a knitted mesh. The reinforcing structure can in particular be a polypropylene mesh, i.e. a mesh with polypropylene threads, in particular monofilament polypropylene threads. Preferably, it is a knitted polypropylene mesh. For example, the mesh can be one of the meshes commercially distributed by the applicant under the brand names Optilene® Mesh, Optilene® Mesh LP and Optilene® Mesh Elastic.

In an alternative embodiment, the reinforcing structure is a grid structure, in particular a metal grid. For example, the reinforcing structure can be a titanium or tantalum grid.

With respect to further suitable materials for the reinforcing structure, the materials mentioned in connection with the insertion aid are incorporated herein by reference in their entirety.

In a further embodiment, the implant, in particular the osteoconductive supporting bodies and/or the insertion aid, further comprises an additive.

The additive can at least partially, in particular only partially, or completely coat the implant, in particular the osteoconductive supporting bodies and/or the insertion aid. Alternatively, a coating containing the additive can at least partially, in particular only partially, or completely coat the implant, in particular the osteoconductive supporting bodies and/or the insertion aid.

Preferably, the additive, together with the osteoconductive supporting bodies, is in the form of a mixture, in particular a heterogenous mixture.

Further preferably, the additive is arranged between the osteoconductive supporting bodies.

Particularly preferably, intermediate spaces formed or present between the osteoconductive supporting bodies are at least partially, in particular only partially, or completely filled with the additive. In this embodiment, the additive can be referred to as a filler.

In a further embodiment, the additive is in particulate form, i.e. in the form of particles, in particular in the form of a bulk material, preferably granules.

In a further embodiment, the additive comprises particles or is in the form of particles having at least one measurement or dimension in a range of 0.1 mm to 4 mm, in particular 0.5 mm to 2 mm, and preferably 1 mm to 1.5 mm. The at least one dimension can in particular be the height and/or the width (thickness) and/or the length and/or the diameter, in particular the average diameter, of the particles.

In a further embodiment, the additive comprises polyhedral particles or is in the form of polyhedral particles. With respect to possible polyhedral configurations of the particles, the polyhedral forms described in connection with the osteoconductive supporting bodies are incorporated herein by reference.

In a further embodiment, the additive comprises non-polyhedral particles or is in the form of non-polyhedral particles. With respect to possible non-polyhedral configurations of the particles, the non-polyhedral forms described in connection with the osteoconductive supporting bodies are incorporated herein by reference.

In a further embodiment, the additive comprises oligopod-shaped particles or is in the form of oligopod-shaped particles. With respect to possible oligopod-shaped configurations of the particles, the oligopod forms described in connection with the osteoconductive supporting bodies are incorporated herein by reference.

The additive is preferably selected from the group consisting of an osteoactive material, an antimicrobial substance such as an antibiotic, anti-inflammatory drugs, a cytostatic, a cytokine, bone morphogenetic protein (BMP), anti-osteoporosis drugs, hyaluronic acid, contrast agents and mixtures of at least two of the aforementioned additives.

An osteoactive substance is particularly preferred as an additive. By means of such an additive, the neogenesis of bone tissue can be stimulated in a particularly advantageous manner, which additionally supports the healing process of a bone defect. An osteoactive substance is advantageous in particular in that osteoblasts can grow into the implant, in particular in a structure formed by the supporting bodies after their compaction, and form osteoids, which then undergo mineralization and become bone.

The osteoactive substance is preferably an osteogenic and/or osteoinductive material.

Moreover, it is preferable for the osteoactive substance to be in vivo degradable or in vivo resorbable.

The osteoactive substance can in particular have an in vivo decomposition time (degradation time) of 1 day to 2 years, in particular 3 days to 10 months, and preferably 1 week to 6 months.

Moreover, the osteoactive substance can in particular have an in vivo resorption time of 1 hour to 1 year, in particular 12 hours to 6 months, and preferably 3 days to 3 months.

Moreover, the osteoactive substance can be a flexible, in particular soft, substance.

Preferably, the osteoactive substance is configured to be more flexible, in particular softer, than the osteoconductive supporting bodies.

Preferably, the osteoactive additive is in direct contact after implantation with a freshly roughened, bleeding bone bed of a bone defect to be treated, preferably an acetabulum, and thus provides favorable prerequisites for the growth of osteoblasts. These can form osteoids, which undergo mineralization and become bone.

In a further embodiment, the osteoactive substance has a content of 5 wt % to 70 wt %, in particular 10 wt % to 50 wt %, and preferably 15 wt % to 25 wt %, based on the total weight of the implant.

The osteoactive additive is preferably selected from the group consisting of proteins such as extracellular protein, polysaccharides such as mucopolysaccharides and/or cellulose derivatives, biological tissue, prepared or purified biological tissue, extracellular matrix, polytrimethylene carbonate, poly-para-dioxanone (poly-1,4-dioxan-2-one), polyhydroxyalkanoate, metal and mixtures of at least two of the aforementioned additives.

The protein can in particular be selected from the group consisting of collagen, gelatin, elastin, reticulin, fibronectin, fibrin, laminin, albumin and mixtures of at least two of the aforementioned proteins. The collagen is preferably collagen type I, collagen type III or a mixture comprising or consisting of collagen type I and collagen type III.

The polysaccharide can in particular be selected from the group consisting of starch, amylose, amylopectin, dextran, dextrin, cellulose, methyl cellulose, ethyl cellulose, hydroxymethyl cellulose, hydroxyethyl cellulose, propyl cellulose, hydroxypropyl cellulose, butyl cellulose, hydroxybutyl cellulose, hydroxyethylmethyl cellulose, hydroxypropylmethyl cellulose, carboxymethyl cellulose, carboxyethyl cellulose, chitin, chitosan, hyaluronic acid, dextran sulfate, heparin, heparan sulfate, chondroitin sulfates such as chondroitin 4-sulfate and/or chondroitin 6-sulfate, dermatan sulfate, keratan sulfate and mixtures of at least two of the aforementioned polysaccharides.

The biological tissue can in particular be an animal or xenogeneic, preferably bovine, equine or porcine, tissue.

The tissue can generally be selected from the group consisting of pericardium, peritoneum, small intestinal submucosa, gastric submucosa, bladder submucosa, uterine submucosa, serosa and mixtures of at least two of the aforementioned tissues.

Preferably, the tissue is selected from the group consisting of pericardium (pericardial sac), pericardium fibrosum, pericardium serosum, epicardium, squamous epithelium, tunica serosa, muscle such as e.g. the myocardium and mixtures of at least two of the aforementioned tissues.

Particularly preferably, the tissue is pericardial tissue, in particular bovine pericardium, i.e. bovine pericardial tissue.

The prepared or purified biological tissue can in particular be a biological tissue freed of non-collagenous components, preferably fats and/or enzymes and/or non-collagenous proteins. Particularly preferably, the prepared or purified tissue is a collagen material produced from bovine pericardium, purified of non-collagenous components, in particular fats, enzymes and non-collagenous proteins, and freeze-dried. Such a material is already commercially distributed by the applicant under the brand name Lyoplant® for dural replacement. With respect to further features of the tissue, the above description is incorporated herein by reference.

The extracellular matrix can in particular be an extracellular matrix of a biological tissue. Preferably, the extracellular matrix is the extracellular matrix of an animal, in particular bovine, equine or porcine tissue. With respect to further features of the tissue, the above explanations are also incorporated herein by reference.

The polyhydroxyalkanoate can in particular be selected from the group consisting of polyglycolide, polylactide, polycaprolactone, poly-3-hydroxybutyrate, poly-4-hydroxybutyrate, copolymers of at least two of the aforementioned polymers and mixtures (blends) of at least two of the aforementioned polymers.

The metal can in particular be titanium and/or tantalum.

In a further embodiment, the osteoactive additive is in uncrosslinked form.

In a further embodiment, the osteoactive additive is in crosslinked form. For example, the osteoactive additive can be a crosslinked protein, in particular crosslinked collagen or crosslinked gelatin.

The cytokine mentioned in connection with the additive can in particular be selected from the group consisting of interferons, interleukins such as interleukin-1β and/or interleukin-6, colony-stimulating factors, chemokines and mixtures of at least two of the aforementioned cytokines.

The bone morphogenetic protein mentioned in connection with the additive can in particular be selected from the group consisting of BMP 1, BMP 2, BMP 3, BMP 3B, BMP 4, BMP 5, BMP 6, BMP 7, BMP 8A, BMP 8B, BMP 10, BMP 15, and mixtures of at least two of the aforementioned bone morphogenetic proteins.

The antimicrobial substance mentioned in connection with the additive can in particular be selected from the group consisting of polyhexamethylene biguanide (PHMB), silver, silver compounds, in particular silver salts, preferably in the form of nanoparticles, and mixtures of at least two of the aforementioned antimicrobial substances.

The antibiotic mentioned in connection with the additive can in particular be gentamycin.

The contrast agent mentioned in connection with the additive can in particular be selected from the group consisting of iodine compounds, heavy metal salts such as barium sulfate, zirconium oxide and mixtures of at least two of the aforementioned contrast agents.

In a further embodiment, the implant is an implant for use in treatment and/or biological reconstruction, in particular lining and/or sealing and/or packing and/or at least partial filling, of a bone defect.

As mentioned above, the bone defect can in particular be an articular defect, preferably a hip joint defect, and particularly preferably an acetabular defect.

In a further embodiment, the treatment is a revision.

In a further embodiment, the implant is a bone implant.

In a further embodiment, the implant is a bone replacement material.

The invention relates according to a second aspect to a kit, in particular a surgical kit, preferably for producing an implant according to a first aspect of the invention and/or for the treatment and/or biological reconstruction, in particular lining and/or sealing and/or packing and/or at least partial filling, of a bone defect.

The bone defect can in particular be an acetabular defect or articular defect, in particular a knee joint defect. Particularly preferably, the bone defect is an acetabular defect.

The kit comprises the following components, spatially separated from one another:
osteoconductive supporting bodies and
an insertion aid.

The kit is characterized in particular in that the insertion aid is configured for insertion of the osteoconductive supporting bodies into a bone defect and for holding together, in particular permanent or temporary holding together, of the osteoconductive supporting bodies, preferably during and/or after their insertion into a bone defect.

In a preferred embodiment, the osteoconductive supporting bodies comprise apatite and/or tricalcium phosphate or consist of apatite and/or tricalcium phosphate.

In a preferred embodiment, the kit further comprises at least one component selected from the group consisting of a bone adhesive, reinforcing structure, endoprosthesis, support shell, spacer implant, fastening element and combinations of at least two of the aforementioned components.

The bone adhesive can e.g. be a bone cement, such as e.g. a calcium phosphate cement, a magnesium phosphate cement or a magnesium-calcium phosphate cement.

With respect to the above-mentioned reinforcing structure, the explanations made in the context of the first aspect of the invention are incorporated herein by reference in their entirety.

The fastening element can e.g. be a bone screw, a bone nail or a thread, in particular a surgical suture material.

The endoprosthesis is preferably an artificial joint socket or an artificial joint socket inlay.

With respect to further features and advantages of the kit, in particular of the osteoconductive supporting bodies and the insertion aid, the explanations made in the context of the first aspect of the invention, which also apply (mutatis mutandis) to the kit, are incorporated herein by reference in their entirety.

According to a third aspect, the invention relates to a method for the treatment and/or biological reconstruction, in particular the lining and/or sealing and/or packing and/or at least partial filling, of a bone defect.

The bone defect can in particular be an acetabular defect or an articular defect, in particular a knee joint defect. Preferably, the bone defect is an acetabular defect.

The method comprises the following step:
placement of an implant according to a first aspect of the invention into a bone defect.

In a preferred embodiment, the method further comprises the following step:
impacting of the placed implant by means of a so-called impactor, i.e. a surgical instrument for compaction, in particular impaction, of the osteoconductive supporting bodies.

In a further embodiment, the method further comprises the following step:
application of a bone cement to the placed, in particular impacted, implant.

In a further embodiment, the method further comprises the following step:
fixing or attachment of an artificial joint socket to the insertion aid, in particular to a covering thereof or to an insertion aid configured as a covering.

In a further embodiment, the method further comprises the following step:
fastening of the artificial joint socket to a bone, preferably to a bone that at least partially surrounds the bone defect.

With respect to further features and advantages of the method, in particular of the implant, the above description, in particular the explanations made in the context of the first aspect of the invention, which also apply (mutatis mutandis) to the treatment method, are incorporated herein by reference in their entirety.

Further features and advantages of the invention can be derived from the claims and the following description of preferred embodiments based on the descriptions of the figures and the accompanying figures. Features of the invention can be implemented individually or in combination with one another respectively. The embodiments described below serve to further explain the invention, without limiting it to said embodiments.

BRIEF DESCRIPTION OF THE FIGURES

FIG. 1 is a schematic top view of a human acetabulum 1, also referred to as the hip joint socket or cotyloid cavity. It is the bony portion of the hip joint formed by the pelvis. The acetabulum is formed by fusion of portions of the ischium, the ilium, and the pubic bone. This fusion is completed at the age of about 6 months.

Under ideal circumstances, the acetabulum and femoral head correspond to each other, i.e. the round femoral head fits precisely into the acetabulum, which embeds and encloses it over a wide area. The hip joint is a multiaxial ball-and-socket joint and is therefore more or less freely moveable in virtually any direction. This ensures high mobility and load-bearing capacity.

The joint-forming parts of the hip joint are surrounded by a connective tissue capsule, whose inner lining, the synovium, continuously produces new synovial fluid. The edge of the bony socket is formed by a ring-shaped joint lip composed of cartilage.

The acetabulum 1 has an anterior acetabular rim 2, also referred to as the anterior horn, and a posterior acetabular rim 4, also referred to as the posterior horn. The acetabular roof 3, which lies between these structures, has a round or an essentially round configuration.

Figure 1:
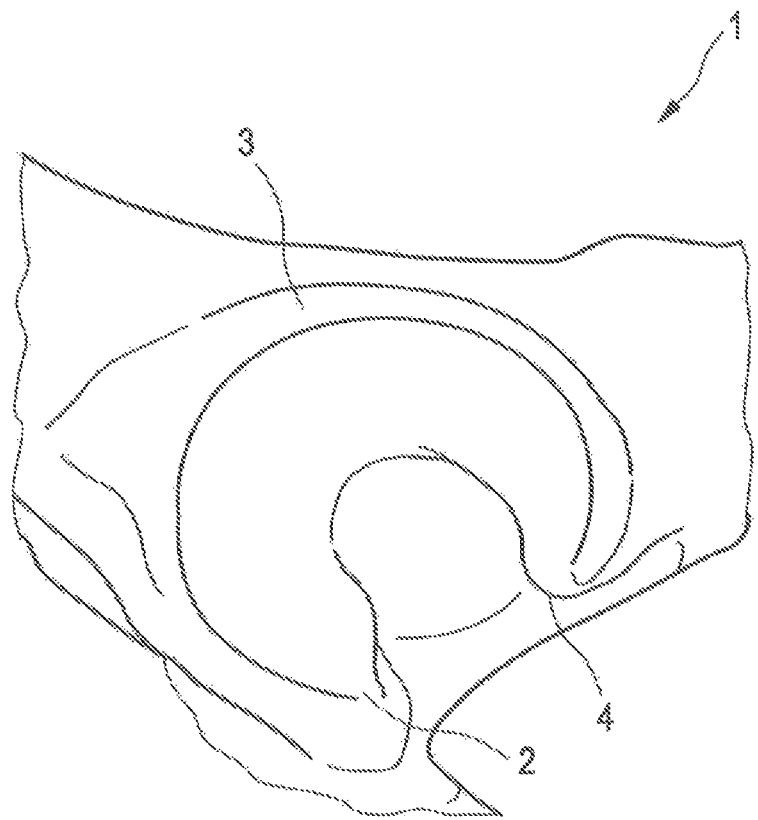
FIG. 1: a top view of a human acetabulum.
Figure 2:
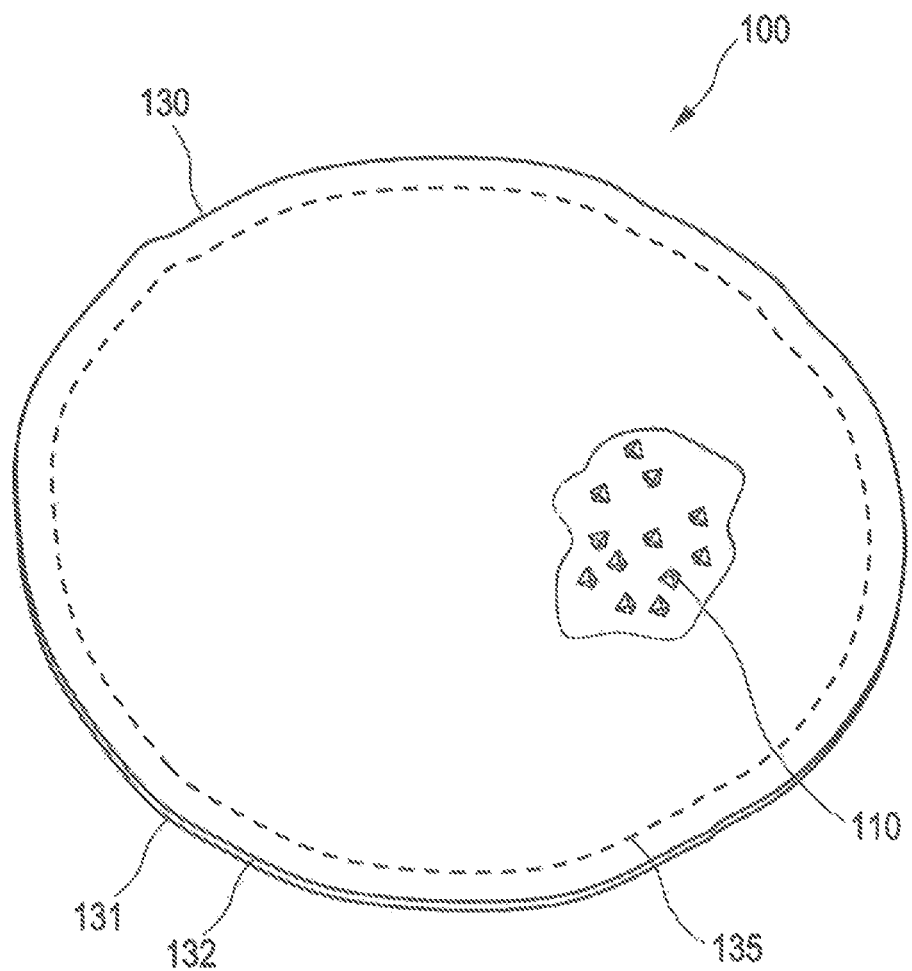
FIG. 2: an embodiment of an implant according to the invention.

FIG. 2 is a schematic diagram of an embodiment of an implant according to the invention 100.

The implant 100 comprises osteoconductive supporting bodies 110 and an insertion aid 130. The insertion aid 130 is configured as a sheath surrounding the osteoconductive supporting bodies 110.

The osteoconductive supporting bodies 110 can for example as shown be in the form of tetrahedra. The tetrahedron-shaped configuration of the supporting bodies 110 facilitates compaction, in particular impaction, of the supporting bodies, allowing a three-dimensional structure to be created, which in particular can reflect the spongiosa of human or animal bone.

The sheath 130 comprises two layers 131; 132 arranged one on top of the other that are connected to each other on their edge by means of a seam 135. The layers 131; 132 as shown can for example have a roughly disk-shaped configuration. The seam 135 can for example be composed of a non-in vivo degradable/non-in vivo resorbable suture material, such as e.g. a polypropylene thread, or an in vivo degradable/in vivo resorbable suture material, such as e.g. a polyglycolide thread.

The two layers 131; 132 sewn to each other enclose a hollow space that is filled at least partially, in particular only partially, with the osteoconductive supporting bodies 110.

The two layers 131; 132 are preferably composed of an in vivo degradable/in vivo resorbable material. The material can in particular be collagen, preferably collagen derived from bovine pericardium. This is advantageous in that it allows new bone tissue to grow into the implant and thus into the bone defect.

The osteoconductive supporting bodies 110 function in a particularly advantageous manner as a guide structure for growing-in bone tissue.

Figure 3:
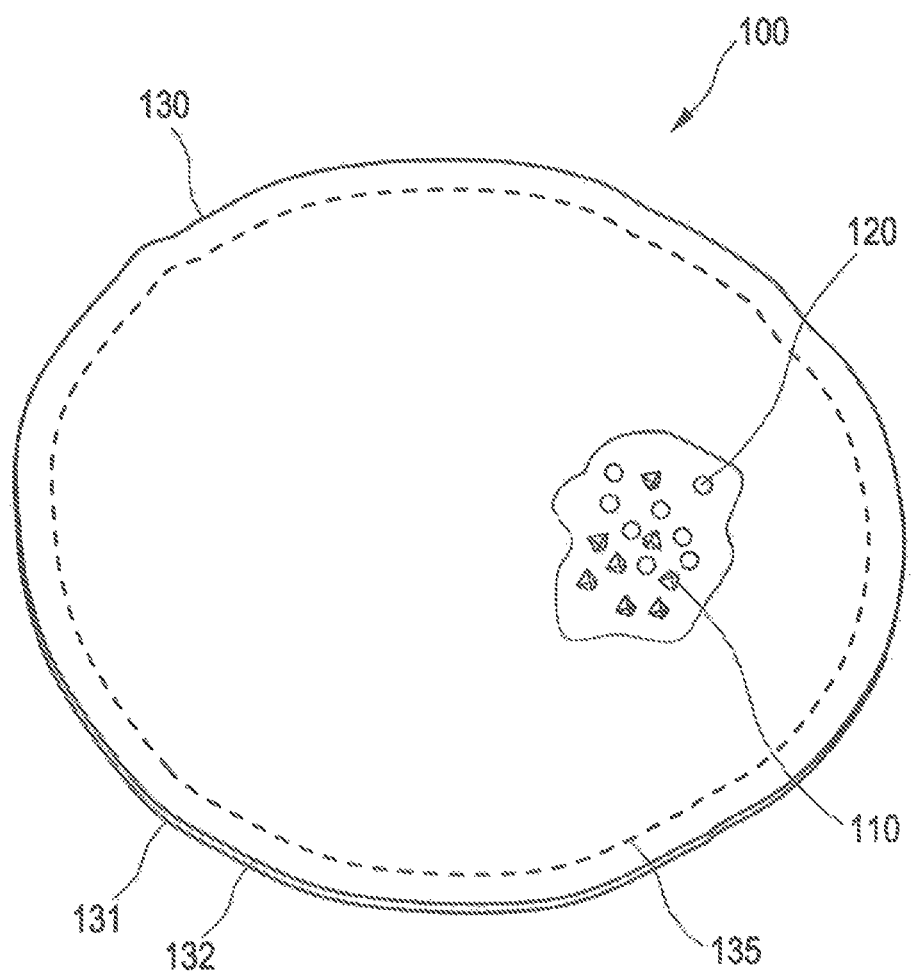
FIG. 3: a further embodiment of an implant according to the invention.

FIG. 3 is a schematic diagram of a further embodiment of an implant according to the invention 100.

The implant 100 comprises osteoconductive supporting bodies 110, an osteoactive substance 120, such as e.g. collagen and/or fibrin, and an insertion aid 130. The insertion aid 130 is configured as a sheath surrounding the osteoconductive supporting bodies 110 and the osteoactive substance 120.

With respect to further features and advantages of the implant 100, in particular the insertion aid or sheath 130, the explanation given for FIG. 2 is incorporated herein by reference in its entirety.

Figure 4:
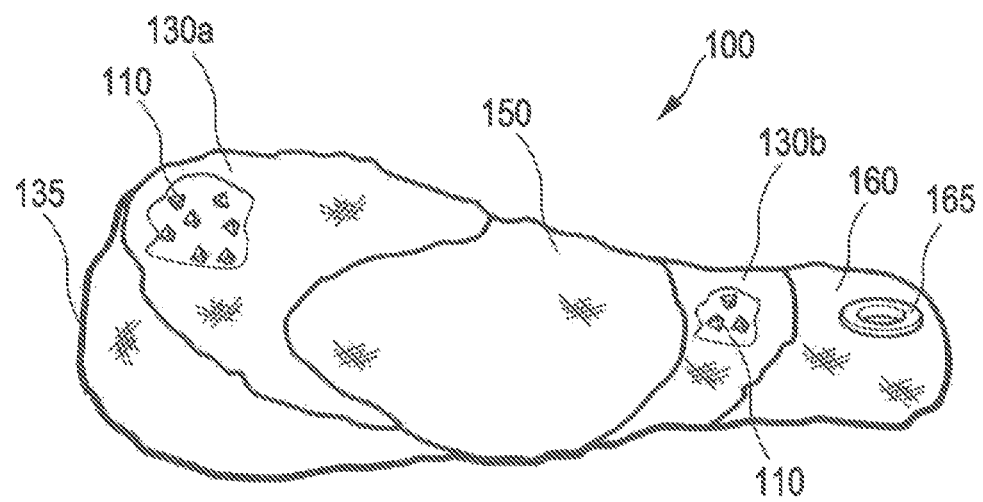
FIG. 4: a further embodiment of an implant according to the invention.

FIG. 4 is a schematic diagram of a further embodiment of an implant according to the invention 100.

The implant 100 comprises osteoconductive supporting bodies 110 and two insertion aids 130a and 130b, which are respectively configured as sheaths. Osteoconductive supporting bodies 110 are contained in the two sheaths 130a; 130b respectively.

The implant further comprises an intermediate area 150 and a lateral area 160.

The lateral area 160 can comprise a fastening device 165, for example in the form of a sleeve. The fastening device 165 is preferably configured to allow fastening of the implant 100 to bone tissue, which is preferably adjacent to a bone defect.

The implant 100 can further comprise a seam 135 for forming the sheaths 130a; 130b and/or reinforcing a seam 135. The seam 135 is preferably configured to run continuously along edge areas of the implant 100 and/or the two sheaths 130a; 130b. The seam 135 can be formed by a shrinkable thread, such as e.g. a thread of poly-4-hydroxybutyrate. This makes it possible in a particularly advantageous manner, for example by radiation-induced shrinkage of the seam 135, to adapt the shape of the implant 100 to a patient-specific shape of a bone defect.

Both the two sheaths 130a; 130b and the sections 150 and 160 respectively can comprise a mesh structure, in particular a knitted mesh structure, for example with monofilament polypropylene threads.

With respect to further features and advantages of the implant 100 shown, the explanation given for FIG. 2 is incorporated herein by reference in its entirety.

Figure 5:
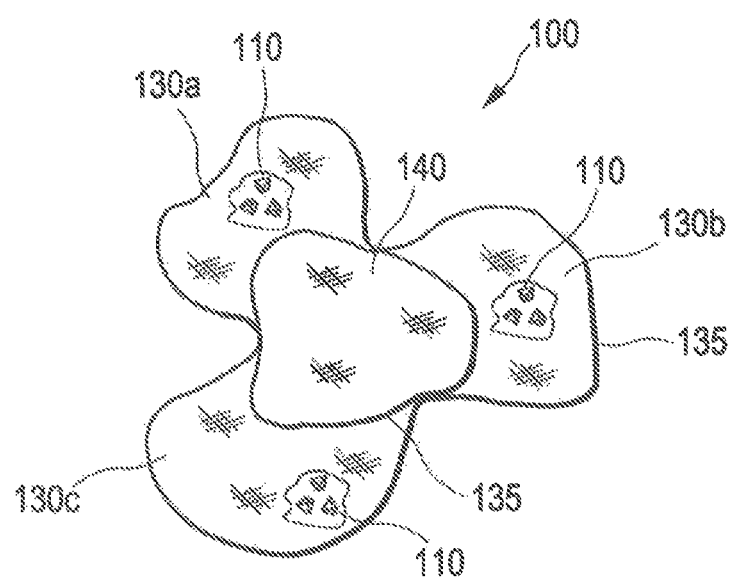
FIG. 5: a further embodiment of an implant according to the invention.

FIG. 5 is a schematic diagram of a further embodiment of an implant according to the invention 100.

The implant 100 comprises a central area 140 and three insertion aids 130a; 130b; 130c configured as sheaths.

The sheaths 130a; 130b; 130c are arranged radially around the central area 140.

The respective sheaths 130a; 130b; 130c are filled at least partially, in particular only partially, with osteoconductive supporting bodies 110.

The central area 140 is preferably configured to be applied to a floor area of a bone defect, while the sheaths 130a; 130b; 130c are preferably configured to be applied to side walls, in particular bone walls that radially surround a bony defect floor.

Both the sheaths 130a; 130b; 130c and the central area 140 respectively comprise a seam 135 running along the edge. In this case as well, the seam 135 can be formed for example by a shrink thread, such as e.g. a thread of poly-4-hydroxybutyrate. By means of selective shrinkage of the seam 135, for example by irradiation, application of the sheaths 130a; 130b; 130c to bone walls radially surrounding the floor of the bone defect can be facilitated.

The sheaths 130a; 130b; 130c and the central area 140 respectively can comprise two mesh layers, in particular knitted mesh layers, arranged on top of each other and connected to each other on the edge by the seam 135.

In this manner, the sheaths 130a; 130b; 130c and the central area 140 define respective hollow spaces. At least the hollow spaces of the sheaths 130a; 130b; 130c can be filled at least partially, in particular only partially, with the osteoconductive supporting bodies 110.

As a whole, the implant 100 is preferably configured in the manner of a triple-bladed propeller, wherein the central area 140 forms the "shaft" and the sheaths 130a; 130b; 130c the "blades" of the propeller.

With respect to further features and advantages of the implant 100 shown in FIG. 5, the explanation given for FIG. 2 is incorporated herein by reference in its entirety.

FIGS. 6a-d show one embodiment each of the osteoconductive supporting bodies 110, each of which facilitates compaction, in particular impaction, for example by means of an impactor.

Figure 6A:
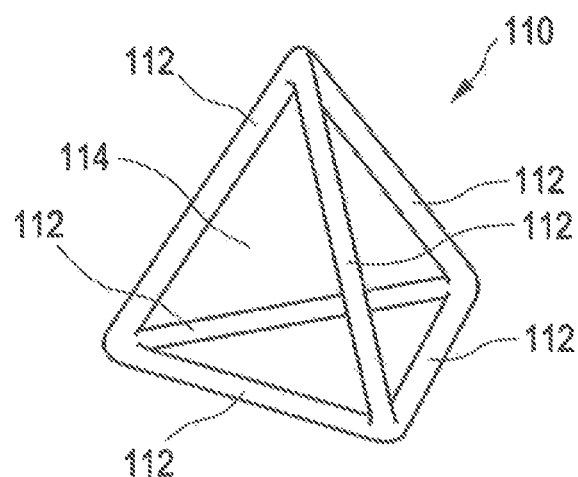
FIG. 6a-d: different embodiments of osteoconductive supporting bodies.

The supporting body 110 shown in FIG. 6a comprises oblong structural elements 112 extending in rectilinear fashion that are assembled to form a tetrahedron-shaped overall structure. The hollow space volume 114 produced by the mutual arrangement of the structural elements 112 contributes in a particularly advantageous manner toward increasing the absolute hollow space volume of a three-dimensional and osteoconductive structure that is obtainable by compaction, in particular impaction, of the osteoconductive supporting bodies. In this manner, for example, it is possible to simulate the spongiosa of human or animal bone, in particular with respect to porosity.

Moreover, the embodiment shown in FIG. 6a facilitates engagement, in particular mutual clamping, of the osteoconductive supporting bodies on application of force and thus the production of a guide structure formed by the supporting bodies.

Figure 6B:
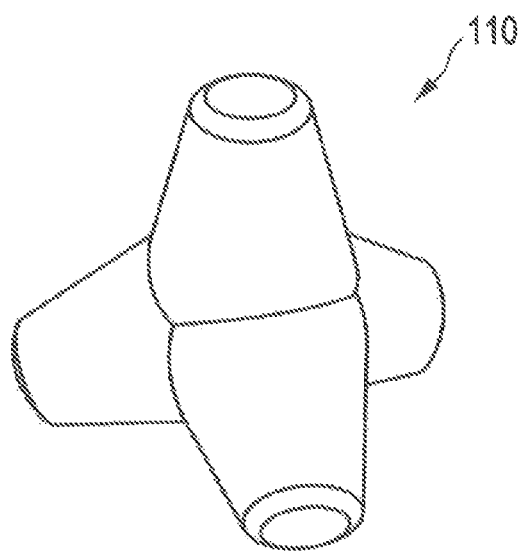

The supporting body 110 shown in FIG. 6b is in the form of a tetrapod. A tetrapod-shaped configuration of the supporting bodies also facilitates engagement, in particular mutual clamping, of the osteoconductive supporting bodies on application of force and thus the production of a guide structure formed by the supporting bodies.

Figure 6C:
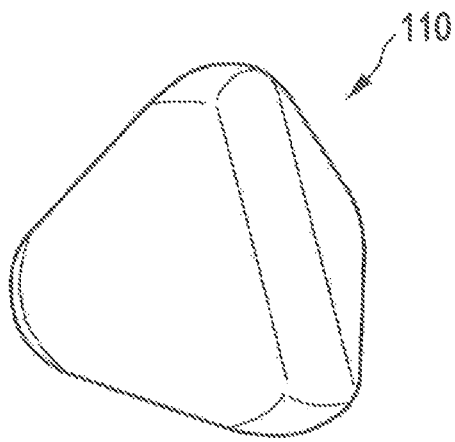

The supporting body 110 shown in FIG. 6c is in the form of a tetrahedron. A tetrahedron-shaped configuration of the supporting bodies also facilitates engagement, in particular mutual wedging, of the osteoconductive supporting bodies on application of force and thus the production of a guide structure formed by the supporting bodies.

Figure 6D:
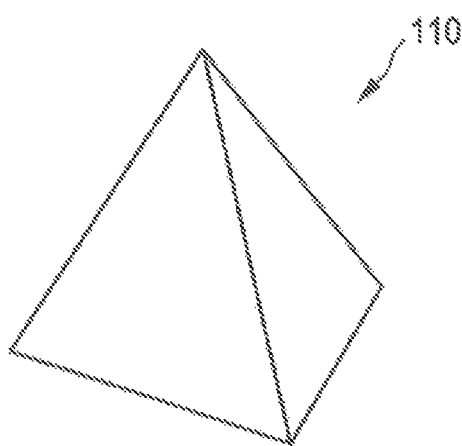

The supporting body 110 shown in FIG. 6d is in the form of a pyramid. A pyramid-shaped configuration of the supporting bodies also facilitates engagement, in particular mutual wedging, of the osteoconductive supporting bodies on application of force and thus the production of a guide structure formed by the supporting bodies.

Figure 7:
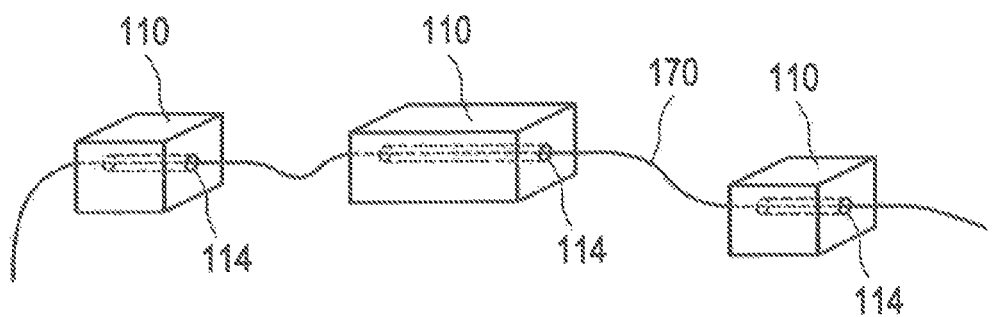
FIG. 7: an embodiment of osteoconductive supporting bodies in combination with a thread-shaped pulling element.

FIG. 7 is a schematic diagram of osteoconductive supporting bodies 110 and an oblong pulling element 170 that can be used in the context of the present invention.

The supporting bodies 110 have respective through openings 114 and can as shown for example have a cuboid configuration. The oblong pulling element 170, as shown, can be guided through the openings 114. In this way, compacting, in particular securing, of the supporting bodies 110 with formation of an osteoconductive guide structure can be achieved. The pulling element 170 is preferably a thread, for example of polypropylene or a polyhydroxyalkanoate, such as e.g. polylactide or polyglycolide.

Figure 8A:
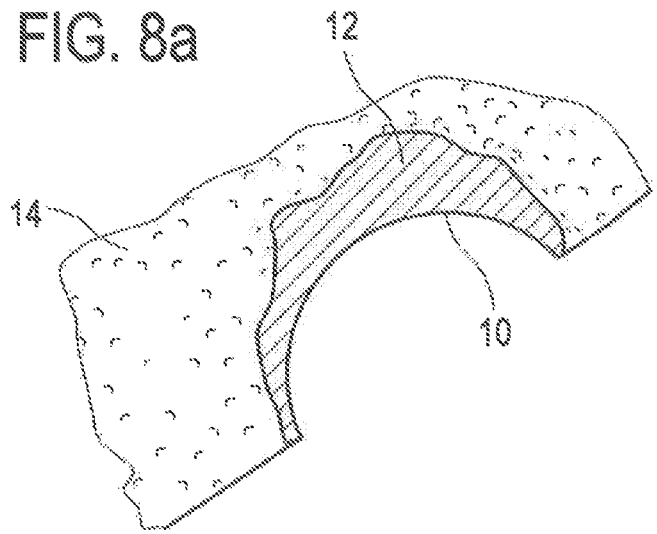
FIG. 8a-c: treatment of a defective acetabulum by means of an implant according to the invention.
Figure 8B:
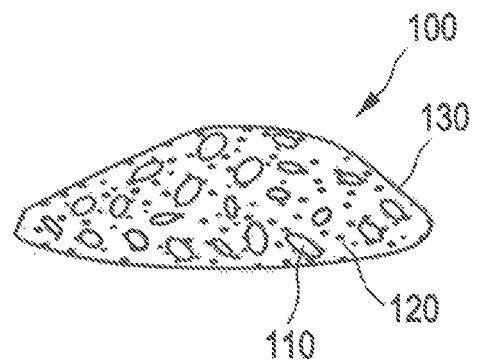
Figure 8C:
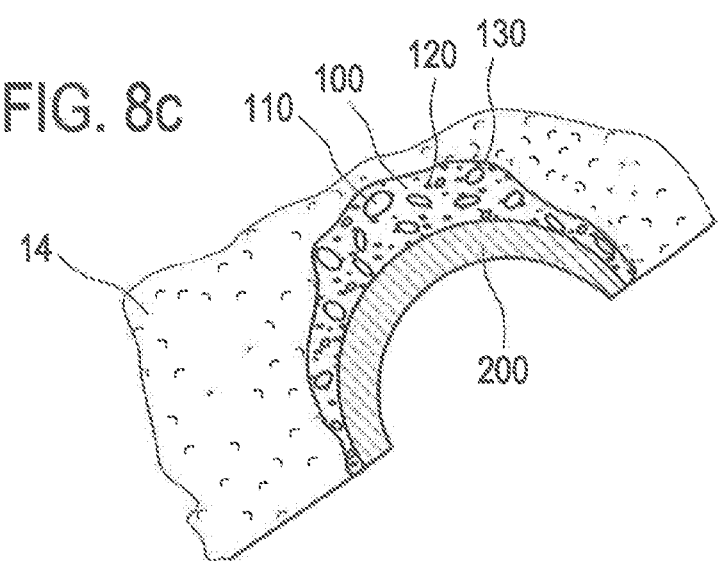

FIGS. 8a-c show a schematic diagram of treatment of a defective acetabulum by means of an implant according to the invention.

FIG. 8a shows an acetabulum 10 with a defect 12 and surrounding bone tissue 14.

The implant 100 comprises osteoconductive supporting bodies 110, an osteoactive substance 120 and an insertion aid 130. The insertion aid 130 is configured as a sheath surrounding the osteoconductive supporting bodies 110 and the osteoactive substance 120 (cf. FIG. 8b).

The implant 100 is first placed in the defective acetabulum 10.

After placement of the implant 100, the osteoconductive supporting bodies 110 are preferably converted to a compacted, in particular impacted, state. This can be carried out for example using a so-called impactor.

An artificial joint socket 200 is then placed on the implant 100 or on bone cement optionally applied to the implant 100 in advance (cf. FIG. 8c).

If the sheath 130 is in vivo degradable or in vivo resorbable and/or configured with open pores, the growth of bone tissue, in particular new bone tissue, into the implant 100 and therefore into the defective acetabulum 10, advantageously occurs within the first four weeks after surgery.

The preferably compacted, in particular impacted, supporting bodies 110 of the implant 100 act as an osteoconductive guide structure for the growing in of bone tissue, while the osteoactive substance 120 enhances and/or stimulates the growing in of bone tissue in a particularly advantageous manner. In this way, the implant 100 can effectively increase the secondary stability of the implanted joint socket 200.

With respect to further features and advantages of the implant 100, the explanation given for FIG. 2 is incorporated herein by reference in its entirety.

Figure 9:
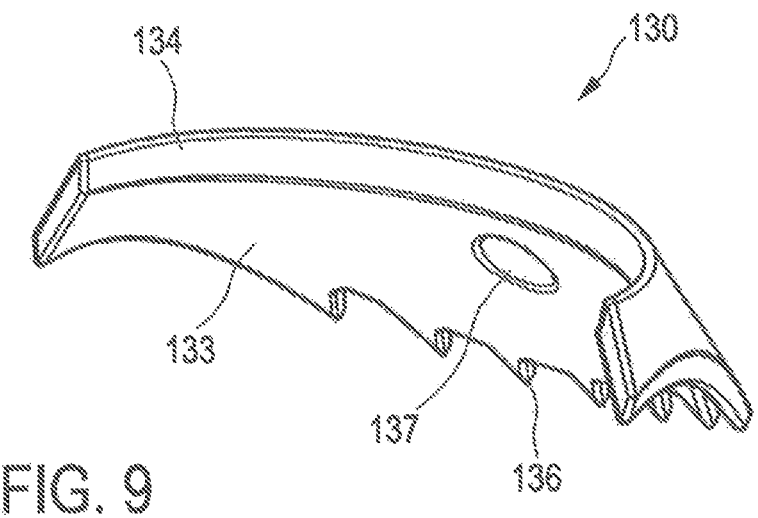
FIG. 9: an embodiment of an insertion aid.

FIG. 9 is a schematic diagram of an insertion aid 130 configured as a plate-shaped covering.

The covering 130 comprises a concave surface 133 to which osteoconductive supporting bodies can be fixed or fastened.

Moreover, the covering comprises 130 a concave connecting area 134. The connecting area 134 is configured to provide a connection to an artificial joint socket, in particular to a convex surface of an artificial socket.

Moreover, the covering 130 comprises anchoring pins 136. The anchoring pins 136 can be driven into a bone, allowing the covering 130 to be anchored in the area of a bone defect to be treated.

The covering 130 further comprises a fastening means opening 137. The opening 137 is configured to accommodate a fastening means, such as e.g. a locking screw. In this manner, an additional possibility for anchoring the covering 130 is provided.

The purpose of both the anchoring pins 136 and the fastening means opening 137 is to achieve primary stability.

Figure 10:
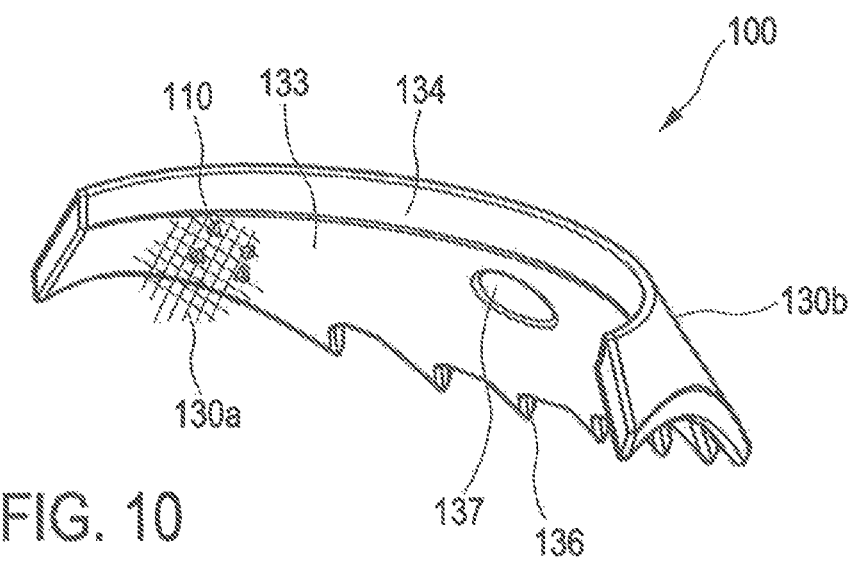
FIG. 10: a further embodiment of an implant according to the invention.

FIG. 10 shows a schematic view of a further embodiment of an implant according to the invention 100.

The implant 100 comprises osteoconductive supporting bodies 110 and an insertion aid configured as a combination of a mesh 130a and a plate-shaped covering 130b.

The mesh 130a preferably fixes the osteoconductive supporting bodies 110 to a concave surface 133 of the covering 130b. For this purpose, the mesh 130a is preferably materially bonded to the surface 133. For example, the mesh 130a can be glued to the surface 133.

Furthermore, the mesh 130a can be a knitted mesh, in particular a knitted polypropylene mesh.

With respect to further features and advantages of the covering 130b, the explanation given in connection with FIG. 9 is incorporated herein by reference in its entirety. The explanations given therein with respect to the covering 130 also apply mutatis mutandis to the covering 130b shown in FIG. 10.

Figure 11:
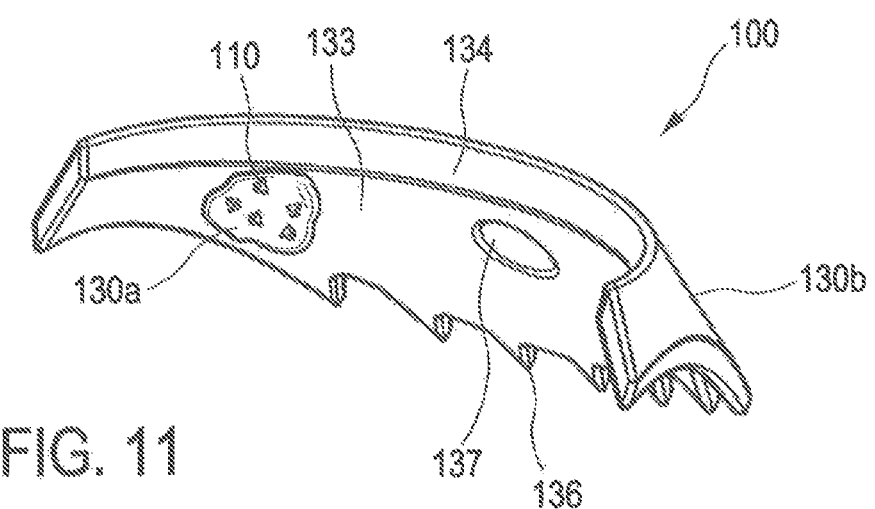
FIG. 11: a further embodiment of an implant according to the invention.

FIG. 11 shows a further embodiment of an implant according to the invention 100.

The implant 100 comprises osteoconductive supporting bodies 110 and an insertion aid configured as a combination of a bonding agent 130a and a plate-shaped covering 130b.

The bonding agent 130a bonds, and preferably glues, the osteoconductive supporting bodies 110 to one another. At the same time, the bonding agent 130a preferably fixes the osteoconductive supporting bodies 110 to a concave surface 133 of the covering 130b.

The bonding agent 130a preferably comprises a protein, in particular collagen and/or gelatin, and/or a polysaccharide, in particular a cellulose derivative and/or hyaluronic acid.

With respect to further features and advantages of the covering 130b, the explanation given in connection with FIG. 9 is incorporated herein by reference in its entirety. The explanations given therein with respect to the covering 130 also apply mutatis mutandis to the covering 130b shown in FIG. 11.

Figure 12:
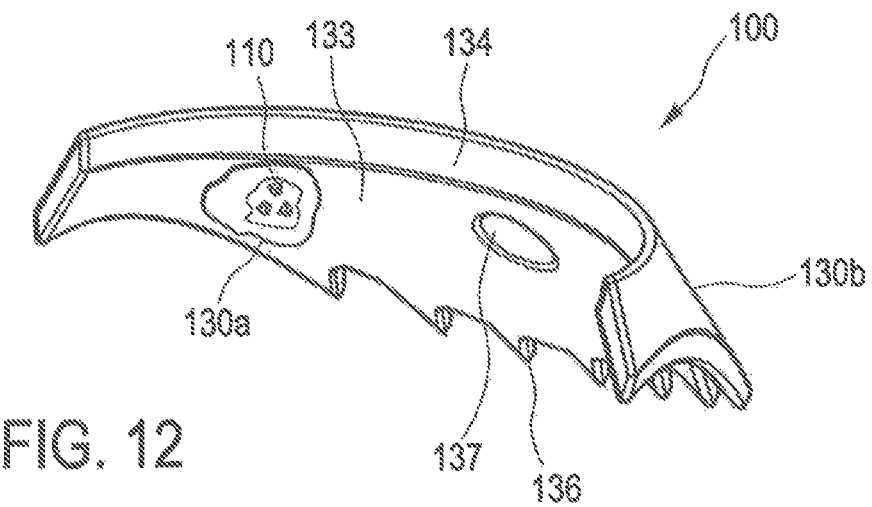
FIG. 12: a further embodiment of an implant according to the invention

FIG. 12 shows a further embodiment of an implant according to the invention 100.

The implant 100 comprises osteoconductive supporting bodies 110 and an insertion aid configured as a combination of a sheath 130a and a plate-shaped covering 130b.

The sheath 130a preferably fixes the osteoconductive supporting bodies 110 to a concave surface 133 of the covering 130b. For this purpose, the sheath 130a is preferably connected to the surface 133 by material bonding. For example, the sheath 130a can be glued to the surface 133. For example, the bonding agent described in FIG. 11 can be used for this purpose.

The sheath 130a can be configured in a mesh-shaped manner or be produced from an animal membrane, preferably pericardium.

With respect to further features and advantages of the covering 130b, the explanation given in connection with FIG. 9 is incorporated herein by reference in its entirety. The explanations given therein with respect to the covering 130 also apply mutatis mutandis to the covering 130b shown in FIG. 12.

Figure 13:
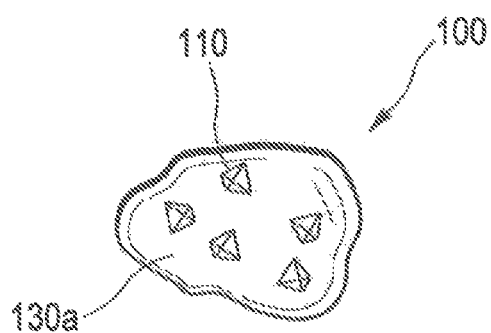
FIG. 13: a further embodiment of an implant according to the invention.

FIG. 13 is a schematic diagram of a further embodiment of an implant according to the invention 100.

The implant 100 comprises osteoconductive supporting bodies 110 and an insertion aid 130 configured as a bonding agent.

The bonding agent 130 bonds, and preferably glues, the osteoconductive supporting bodies 110 to one another.

In a particularly advantageous manner, the implant 100 shown can easily be adapted during surgery to a bone defect to be treated with respect to shape and quantity.

With respect to further features and advantages of the implants shown in the figures, the general description is incorporated herein by reference in its entirety.

The invention claimed is:

1. An implant for treating a bone defect, comprising: osteoconductive supporting bodies and an insertion aid, wherein the insertion aid is designed for insertion of the osteoconductive supporting bodies into a bone defect and for holding together the osteoconductive supporting bodies, the insertion aid is configured as a combination of a textile flat structure and a bonding agent, wherein the osteoconductive supporting bodies are bonded to one another by means of the bonding agent with formulation of a pastry or kneadable preparation, wherein the bonding agent comprises an amount of liquid diluent of 60 wt % to 90 wt %, based on the total weight of the bonding agent, further wherein the bonding agent is configured as an adhesive, wherein the adhesive comprises an oligopeptide having 2 to 100 amino acid units and a terminal oligolactam and/or a nitrogen-functionalized polysaccharide.

2. The implant of claim 1, wherein the osteoconductive supporting bodies comprise apatite and/or tricalcium phosphate or consist of apatite and/or tricalcium phosphate.

3. The implant of claim 2, wherein the apatite and/or the tricalcium phosphate has a porosity of 1% to 50%.

4. The implant of claim 2, wherein the apatite and/or the tricalcium phosphate is/are not configured to be porous.

5. The implant of claim 2, wherein the apatite is selected from the group consisting of hydroxyapatite, fluorapatite, chlorapatite, carbonate-fluorapatite and mixtures of at least two of thereof.

6. The implant of claim 2, wherein the tricalcium phosphate is selected from the group consisting of alpha-tricalcium phosphate, beta-tricalcium phosphate and a mixture of alpha-tricalcium phosphate and beta-tricalcium phosphate.

7. The implant of claim 1, wherein the textile flat structure is a mesh.

8. The implant of claim 1, wherein the bonding agent comprises a protein and/or a polysaccharide.

9. The implant of claim 1, wherein the bonding agent comprises glycerol.

10. The implant of claim 1, wherein the diluent is glycerol and/or water.

11. The implant of claim 1, wherein the bonding agent comprises carboxymethyl cellulose and glycerol.

12. The implant of claim 1, wherein the bonding agent is configured as an adhesive.

13. The implant of claim 8, wherein the protein is collagen and/or gelatin.

14. The implant of claim 8, wherein the polysaccharide is a cellulose derivative and/or hyaluronic acid.

15. The implant of claim 14, wherein the cellulose derivative is carboxymethyl cellulose.

* * * * *